United States Patent
Dalton et al.

(10) Patent No.: US 10,266,878 B2
(45) Date of Patent: Apr. 23, 2019

(54) GENOMIC ANALYSIS DEVICE AND METHODS OF USE

(71) Applicant: GenCell Biosystems Ltd., Raheen, County Limerick (IE)

(72) Inventors: Mark Dalton, Limerick (IE); John Daly, Tralee (IE); Mark McCabe, Dublin (IE); Padraig Walsh, Nenagh (IE); Kevin Daulnay, Dublin (IE); David McGuire, Enniscorthy (IE); Maria Kerin, Killarney (IE); Maria O'Connor, Croom (IE); Colin King, Naas (IE); Keith Mooney, Dooradoyle (IE)

(73) Assignee: GENCELL BIOSYSTEMS LTD., Raheen, Country Limerick (IE)

( * ) Notice: Subject to any disclaimer, the term of this patent is extended or adjusted under 35 U.S.C. 154(b) by 137 days.

(21) Appl. No.: 15/319,361

(22) PCT Filed: Aug. 3, 2015

(86) PCT No.: PCT/IB2015/055903
§ 371 (c)(1),
(2) Date: Dec. 15, 2016

(87) PCT Pub. No.: WO2016/020838
PCT Pub. Date: Feb. 11, 2016

(65) Prior Publication Data
US 2017/0130262 A1   May 11, 2017

Related U.S. Application Data

(60) Provisional application No. 62/033,279, filed on Aug. 5, 2014, provisional application No. 62/032,882, filed on Aug. 4, 2014.

(51) Int. Cl.
*G01N 15/06* (2006.01)
*G01N 33/00* (2006.01)
(Continued)

(52) U.S. Cl.
CPC .......... *C12Q 1/6816* (2013.01); *A01K 45/007* (2013.01); *B01L 3/50851* (2013.01);
(Continued)

(58) Field of Classification Search
CPC ........ G01N 15/06; G01N 33/00; G01N 33/48; G01N 35/00
(Continued)

(56) References Cited

U.S. PATENT DOCUMENTS 6,103,463 A * 8/2000 Chetverin ............ B01J 19/0046
435/6.12
8,465,707 B2   6/2013 Curran et al.
(Continued)

FOREIGN PATENT DOCUMENTS

WO   WO 2012/011091 A2   1/2012
WO   WO 2013/074796 A1   5/2013
(Continued)

*Primary Examiner* — Brian J. Sines
(74) *Attorney, Agent, or Firm* — Kathleen Y. Rao; Bret E. Field; Bozicevic, Field & Francis LLP

(57) ABSTRACT

Aspects of the present disclosure include a complete genomic analysis device and methods of use thereof for high throughput genomic analysis of biological samples.

18 Claims, 14 Drawing Sheets

(51) Int. Cl.
  *G01N 33/48* (2006.01)
  *G01N 35/00* (2006.01)
  *C12Q 1/6816* (2018.01)
  *C12Q 1/6806* (2018.01)
  *C12Q 1/6879* (2018.01)
  *A01K 45/00* (2006.01)
  *B01L 3/00* (2006.01)
(52) U.S. Cl.
  CPC ........ B01L 3/50853 (2013.01); *C12Q 1/6806* (2013.01); *C12Q 1/6879* (2013.01); *G01N 35/0099* (2013.01); *B01L 2300/0829* (2013.01); *B01L 2300/1822* (2013.01)
(58) Field of Classification Search
  USPC ..................... 422/50, 68.1; 436/43, 174, 180
  See application file for complete search history.

(56) References Cited

U.S. PATENT DOCUMENTS

2003/0211504 A1* 11/2003 Fechtel .................. G06F 19/22
                                                              435/6.11
2005/0118665 A1*  6/2005 Zhou ........................ C12Q 1/00
                                                                435/23
2009/0099029 A1*  4/2009 Samuels ............ C12K 14/4713
                                                                 506/9
2010/0120635 A1   5/2010 Davies et al.
2012/0045765 A1   2/2012 Curran et al.
2014/0080165 A1   3/2014 Phelps et al.
2015/0238920 A1   8/2015 Curran et al.
2016/0033370 A1   2/2016 Barrett et al.

FOREIGN PATENT DOCUMENTS

| WO | WO 2013/111016 A2 | 8/2013 |
| WO | WO 2014/083435 A2 | 6/2014 |
| WO | WO 2014/188281 A2 | 11/2014 |
| WO | WO 2014/207577 A2 | 12/2014 |
| WO | WO 2015/075560 A2 | 5/2015 |
| WO | WO 2015/075563 A2 | 5/2015 |
| WO | WO 2015/120398 A2 | 8/2015 |
| WO | WO 2016/020837 A1 | 2/2016 |
| WO | WO 2016/020839 A1 | 2/2016 |

* cited by examiner

GENOMIC ANALYSIS DEVICE AND METHODS OF USE

CROSS-REFERENCE TO RELATED APPLICATIONS

Pursuant to 35 U.S.C. § 119 (e), this application claims the benefit of priority to U.S. Provisional Patent Application Ser. No. 62/032,882, filed Aug. 4, 2014, and U.S. Provisional Patent Application Ser. No. 62/033,279, filed Aug. 5, 2014, the disclosures of which applications are hereby incorporated by reference herein in their entirety.

INTRODUCTION

Genomic analysis is applicable to many diverse fields, including agriculture, epidemiology, molecular genetics, and the health industry.

Genomic analysis is used for example in genotyping a biological sample, which is a process in which DNA sequences are utilized to define biological populations by use of molecular tools. These molecular tools generally determine the genetic makeup (entire set of genes) of a cell, an organism, or an individual with reference to a single trait, set of traits, or an entire complex of traits. A trait may exist in two allelic forms; one is dominant (e.g. A) and the other recessive (e.g. a). Based on this, there could be three possible genotypes for a particular trait: AA (homozygous dominant), Aa (heterozygous), and aa (homozygous recessive). Genotyping can be performed through a variety of different methods, depending on the variants of interest and resources available.

In agriculture, genetic assays for gender sorting are of value. In these processes, nucleic acid sequences are utilized to define biological gender populations using molecular tools. The current market of avian gender sorting is preformed manually.

One of the most common methods for genomic analysis is PCR detection (polymerase chain reaction). The method relies on thermal cycling, DNA polymerase, primers (short DNA fragments complimentary to the targeted region of interest). Thermal cycling consists of repeated cycles of heating and cooling of the reaction for DNA melting and enzymatic replication of the DNA. The replicated DNA is detectable by many methods, the most common being through the use of fluorescently labeled probes that are specific to each allele. To date, some advances have been made to fully automate the process, but typically genotyping requires several instruments and manual processes to complete. Genotyping is generally performed in 96 static well plates with typical volumes ranging from 1 microliter to 20 microliters.

SUMMARY

The invention is a complete system for performing a high throughput genomic analysis assay carried out in composite liquid cells (CLC). As used herein, "composite liquid cell" refers to a configuration in which an aliquot of an aqueous sample (or target fluid) is encapsulated in a hydrophobic encapsulating fluid, both of which sit on the free surface of a hydrophobic carrier fluid that is immiscible with both the aqueous sample and the encapsulating fluid. In the present system, CLCs are processed and manipulated at ambient pressure, although the liquids that make up the CLCs may be dispensed to or retrieved from the CLCs under either positive or negative pressure respectively.

Aspects of the present disclosure include a complete genomic analysis device, the device comprising: a thermal chip module comprising multiple self-contained composite liquid cell (CLC) locations; a CLC production station configured to access each self-contained CLC location of the thermal chip module; a sample receiving location; a reagent receiving location; a robotically controlled liquid handler configured to transfer liquid between the sample receiving location, the reagent receiving location, and the thermal chip module; and an interrogation station configured to interrogate each self-contained CLC location of the thermal chip module.

In certain embodiments, the thermal chip module comprises from 1400 to 3000 self-contained CLC locations.

In certain embodiments, the device comprises a mechanically actuated lid for the thermal chip module.

In certain embodiments, the reagent receiving location is configured to receive an assay plate and a master mix plate.

In certain embodiments, the reagent receiving location is configured to receive multiple assay plates.

In certain embodiments, the assay and master mix plates are standard laboratory plates.

In certain embodiments, the robotically controlled liquid handler comprises interchangeable heads configured for sample dispense, assay dispense, and master mix dispense operations.

In certain embodiments, the CLC production station is configured to dispense carrier and encapsulating fluid into the self-contained CLC locations and wash the self-contained CLC locations.

In certain embodiments, the device comprises a fluidics module comprising liquid reservoirs for system fluids and waste collection.

In certain embodiments, the device is operatively coupled to a barcode scanner.

In certain embodiments, the interrogation station is configured to detect an optical signal.

In certain embodiments, the interrogation station is configured to transmit excitation light to and collect emission light from each self-contained CLC location in the thermal chip module.

In certain embodiments, the interrogation station comprises a camera based detection system.

In certain embodiments, the excitation light is from a LED.

In certain embodiments, the interrogation station detects multiple wavelengths of light.

In certain embodiments, the device is a genotyping device. In certain embodiments, the sample receiving location is configured to receive a sample plate. In certain embodiments, the sample plate is a standard laboratory plate. In certain embodiments, the sample receiving location is configured to receive multiple sample plates.

In certain embodiments, the device is an avian sexing device. In certain embodiments, the sample receiving location is operatively connected to an egg sampling unit (ESU) configured to obtain biological samples from multiple avian eggs. In certain embodiments, the self-contained CLC locations of the thermal chip module are arranged in multiple clusters that are spaced at a pitch configured for receiving the biological samples from the multiple avian eggs. In certain embodiments, each of the multiple clusters comprises from 2 to 40 self-contained CLC locations. In certain embodiments, the thermal chip module comprises 84 clusters each comprising 17 self-contained CLC locations. In certain embodiments, the thermal chip module comprises an upper lid and a lower lid, wherein the upper lid and lower lid comprise holes corresponding to the self-contained CLC locations, wherein the upper lid is fixed to the thermal chip module such that the holes are aligned with the corresponding self-contained CLC locations and the lower lid is mounted on a mechanism that can be actuated to offset the alignment of the holes with the upper lid to close the holes in the upper lid.

Aspects of the present disclosure include methods of genetically analyzing a plurality of biological samples, the method comprising: introducing a plurality of biological samples into the sample location of a device as described herein; operating the device to perform a genotyping assay by: (i) generating a CLC genomic analysis reaction sample for each of the plurality of biological samples in a corresponding self-contained CLC location of the thermal chip module; (ii) performing a reaction in the CLC genomic analysis reaction sample by running a thermal program on the thermal chip module; and (iii) detecting a signal from each of the CLC genomic analysis reaction samples in the corresponding self-contained CLC locations of the thermal chip module with the interrogation station; wherein the signal detected for each of the CLC genomic analysis reaction samples is indicative of a genetic characteristic of each of the plurality of biological samples.

In certain embodiments, each of the CLC genomic analysis reaction samples is in a total volume of 300 nl.

In certain embodiments, the method further comprises introducing into the device an assay plate comprising a reagent for performing the genotyping assay.

In certain embodiments, multiple different genomic analysis assays are performed.

In certain embodiments, a different assay plate is introduced into the device for each of the multiple different genomic analysis assays performed.

In certain embodiments, the generating step comprises: operating the CLC production station to dispense a carrier fluid and an encapsulating fluid into each self-contained CLC location of the thermal chip module; and operating the robotically controlled liquid handler to: dispense each of the plurality of biological samples into a corresponding self-contained CLC location of the thermal chip module; dispense an assay reagent into each self-contained CLC location of the thermal chip module; and dispense a master mix reagent into each self-contained CLC location of the thermal chip module.

In certain embodiments, the genomic analysis assay is a genotyping assay.

In certain embodiments, the genomic analysis assay is an avian sexing assay.

BRIEF DESCRIPTION OF THE DRAWINGS

Aspects of the disclosure may be best understood from the following detailed description when read in conjunction with the accompanying drawings. Included in the drawings are the following figures.

DETAILED DESCRIPTION

Figure 1:
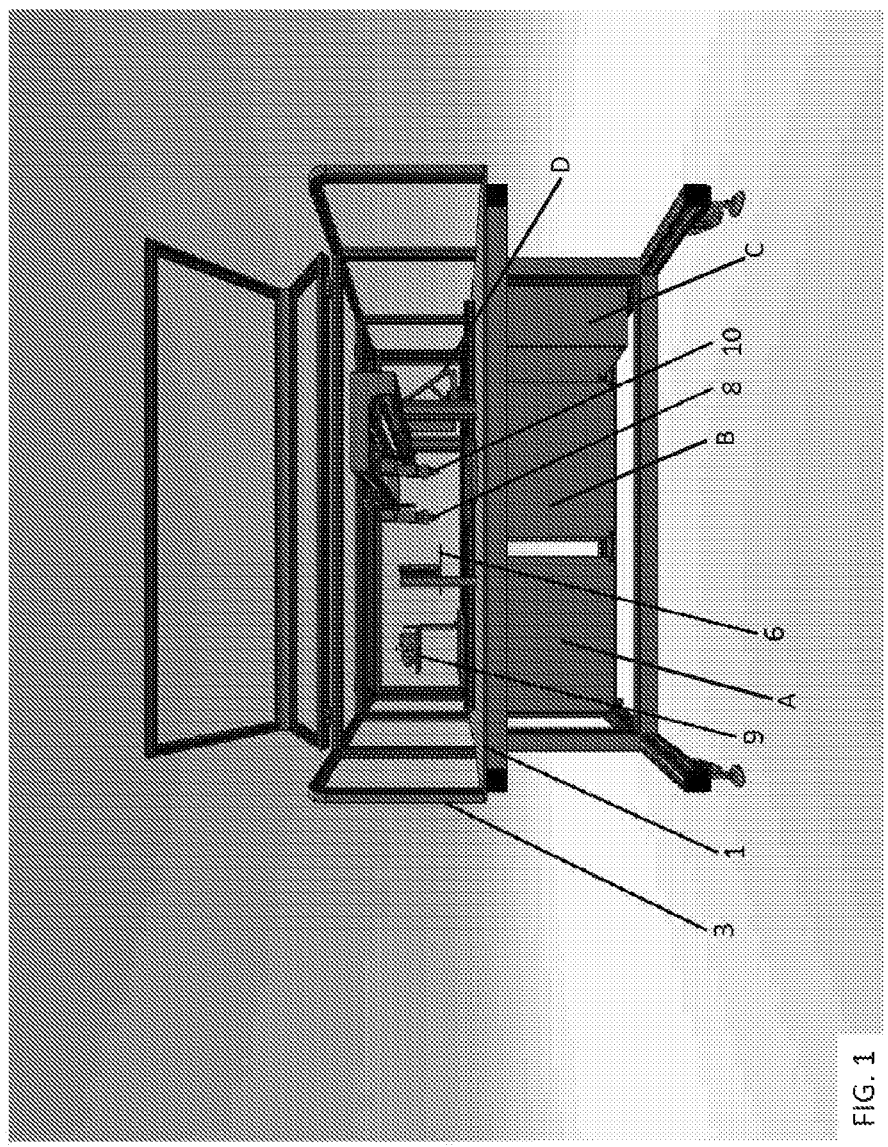
FIGS. 1 to 6 show examples of devices according to aspects of the present disclosure.

As summarized above, aspects of the invention include complete systems for performing a high throughput genomic analysis assay carried out in composite liquid cells (CLC). As used herein, "composite liquid cell" refers to a configuration in which an aliquot of an aqueous sample (or target fluid) is encapsulated in a hydrophobic encapsulating fluid, both of which sit on the free surface of a hydrophobic carrier fluid that is immiscible with both the aqueous sample and the encapsulating fluid. In the present system, CLCs are processed and manipulated at ambient pressure, although the liquids that make up the CLCs may be dispensed to or retrieved from the CLCs under either positive or negative pressure respectively.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Devices and Methods of Using Same for Genetic Assays

As summarized above, aspects of the invention include a complete genomic analysis device. As the devices are complete genomic analysis preparation devices, they include all components necessary to perform a genomic analysis from an initial biological sample containing a nucleic acid component, e.g., a cell, a tissue, a purified or processed sample, etc. Accordingly, the devices are configured such that an initial biological sample can be introduced into the device and a complete genomic analysis protocol can be performed on the device and the results retrieved by a user, with little if any user interaction with the device between the time of sample introduction and return of the results. The devices include all liquid handling and other components necessary to perform a genomic analysis, as reviewed in greater detail below. The devices are automated, in that they are configured so that at least some, if not all, steps of a given genomic analysis protocol may occur without human intervention, beyond introduction of the biological sample into the device, loading of any requisite reagents and input of information, and activating the device to perform the genomic analysis from the biological sample. Steps of a genomic analysis protocol that may be automated in the devices include, but are not limited to: liquid transfer steps, reagent addition steps, thermal cycling steps, sample interrogation steps, etc.

The devices can be of any size convenient for housing the necessary components and interfacing with external components should this be desired. In some instances the device has a depth ranging from 1 to 2 meters, such as 1.3 to 1.6 meters, e.g., 1.4 meters; a width ranging from 2 to 3 meters, such as 2.2 to 2.5 meters, e.g., 2.3 meters; and a height ranging from 1 to 2.5 meters, such as 1.4 to 2 meters, e.g., 1.5 meters. The weight of the device may vary, and in some instances ranges from 250 to 500 kg, such as 300 to 400 kg, e.g., 350 kg.

As summarized above, devices according to embodiments of the invention include at least a thermal chip module, a composite liquid cell (CLC) production station, a sample receiving location, a reagent receiving location, a robotically controlled liquid handler configured to transfer liquid between the sample receiving location, the reagent receiving location, and the thermal chip module thermal chip module, and an interrogation station configured to interrogate each self-contained CLC location of the thermal chip module.

Each of these components or subunits of the device will now be described in greater detail, as will additional components and subunits.

Thermal Chip Module

Figure 8:
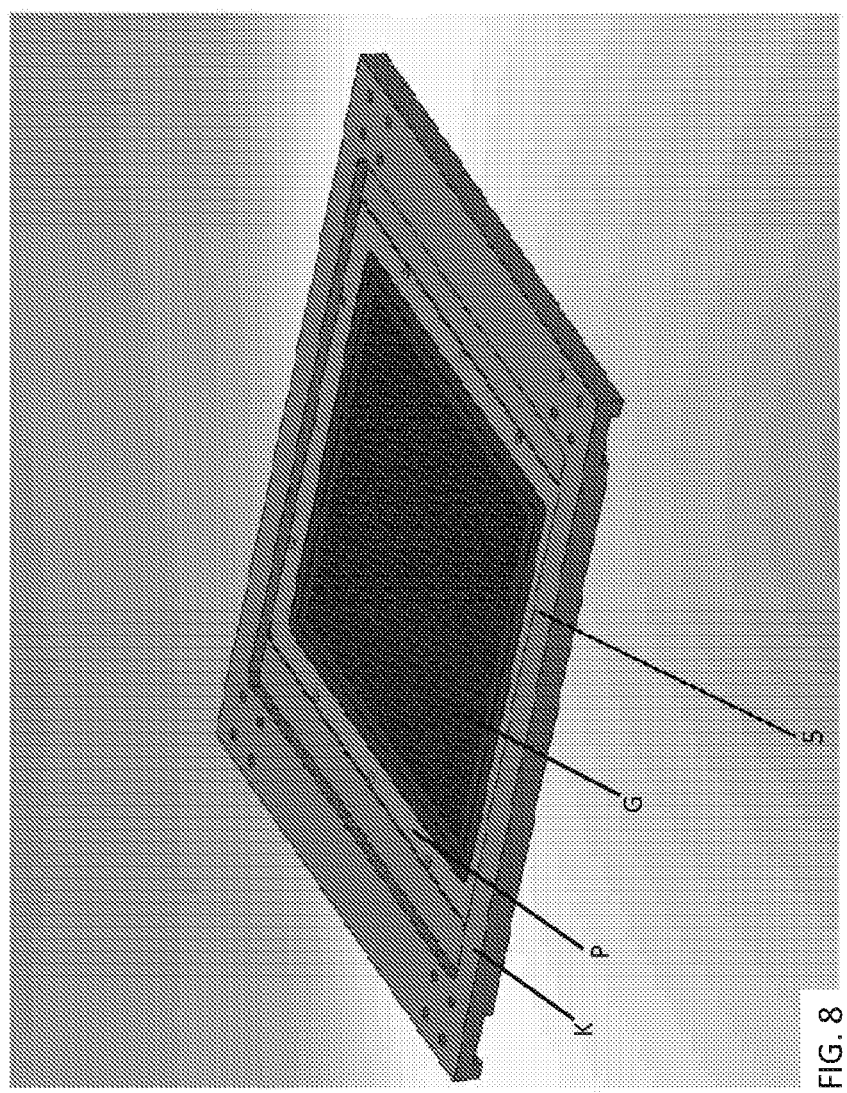
FIG. 8 shows an example of a thermal chip module according to aspects of the present disclosure.

As summarized above, devices described herein include a thermal chip module. An example of a thermal chip module is shown in FIG. 8 (described in further detail below) and is shown in a device according to aspects of the present disclosure as element (5) in FIGS. 2 and 5. The devices may include a single thermal chip module, or two thermal chip modules. Thermal chip modules are plate or chip type structures that include one or more self-contained locations (e.g., wells), where each self-contained location is configured to accommodate a CLC (also referred to as a self-contained CLC location). Each self-contained CLC location is open at the top to provide for liquid access to a CLC present therein. The volume defined by a given self-contained CLC location of a thermal chip module may vary, and in some instances ranges from 2 µl to 1 ml, such as 5 µl to 20 µl. The cross-sectional shape of a given self-contained CLC location may also vary, where cross-sectional shapes of interest include, but are not limited to, cylindrical, conical, frustoconical, circular, rectangular (including square), triangular, etc. While the dimensions of each self-contained CLC location may vary, in some instances the self-contained CLC locations have a longest cross-sectional dimension (e.g., diameter) ranging from 1 mm to 25 mm, such as 2.5 mm to 10 mm and a depth ranging from 1 mm to 30 mm, such as 3 to 20 mm. The number of self-contained CLC locations present in a given thermal chip module may also vary, ranging in some instances from 200 to 10,000, such as 500 to 5,000 or 1,400 to 2,400. In some embodiments, the number of self-contained CLC locations is a multiple of 96 or 384, e.g., 2304, e.g., in embodiments where correspondence with conventional multi-well plates is desired. In certain specific embodiments, the self-contained CLC locations on the thermal chip module are present in multiple groups or clusters that are spaced to accommodate receiving samples derived from multiple biological source having a particular spacing (or pitch), e.g., samples harvested from a sampling unit for avian eggs (described in further detail below).

FIG. 8 shows an example of a thermal chip module (5) that includes a chip holder (K), a chip insulator (P) and the chip that defines the self-containing CLC locations (G). The components of a thermal chip module may be made of any convenient material. Materials of interest include, but are not limited to thermally conductive materials, e.g., composites, ceramics, and metals, including aluminum. While the dimensions of a thermal chip module may vary, in some instances the thermal chip module has a length ranging from 10 cm to 400 cm, such as 10 cm to 200 cm; a width ranging from 10 cm to 400 cm, such as 10 cm to 200 cm and a height ranging from 10 mm to 50 mm, such as 20 mm to 40 mm.

As mentioned above, each self-contained CLC location is configured to accommodate a carrier fluid, a target fluid, and an encapsulating fluid that together form a CLC. By CLC is meant a triphasic fluid arrangement that is a combination of at least three substantially mutually immiscible fluids having three different densities. The first fluid is a carrier fluid which is the densest of the three substantially mutually immiscible fluids; the second fluid is an encapsulating fluid which is the least dense of the substantially mutually immiscible fluids; and the third fluid is a target fluid (sometimes referred to as a "sample") which has a density that is less than the first fluid and greater than the second fluid. A CLC may take a variety of different forms in the self-contained CLC location, where in some embodiments the target fluid is encased in the encapsulating fluid and where the resulting roughly spherical structure is present on the surface of the carrier fluid. In this form, the carrier fluid is not fully covered by the encapsulating fluid. In other embodiments, the target fluid is encased (or encapsulated) between the carrier fluid and the encapsulating fluid such that entire surface of the carrier fluid in the self-contained CLC location is covered by the encapsulating fluid.

In certain embodiments, the target fluid is an aqueous fluid, where in some embodiments the aqueous fluid contains a biological sample, reagent, buffer, or other prescribed element of a genetic assay. Examples of components that can be present in the aqueous fluid include, but are not limited to: cells, nucleic acids, proteins, enzymes, biological sample (e.g., blood, saliva, etc.), buffers, salts, organic material, and any combination thereof.

In certain embodiments, the density of the carrier fluid is from 1,300 to 2,000 kg/m$^3$, the density of the target fluid is from 900 to 1,200 kg/m$^3$, and the density of the encapsulating fluid is from 700 to 990 kg/m$^3$. The difference in density between the carrier fluid and the target fluid or between the target fluid and the encapsulating fluid is from 50 to 2000 kg/m$^3$. In general, the difference in density between the three substantially mutually immiscible fluids should be sufficient to prevent substantial intermixing between any two of them under the conditions in which they are to be stored and/or used in any downstream process or analytical assay. Additional details regarding carrier, encapsulating and target fluids may be found in U.S. Pat. Nos. 8,465,707 and 9,080,208; as well as United States Patent Application Publication No. 20140371107; and Published PCT Application Nos: WO2014/083435; WO2014/188281; WO2014/207577; WO2015/075563; WO2015/075560; the disclosures of which applications are herein incorporated by reference.

In certain embodiments, carrier fluid and/or the encapsulating fluid is an oil. For example, in certain embodiments, the carrier and/or the encapsulating fluid can be a silicone oil, a perfluorocarbon oil, or a perfluoropolyether oil. Thus, in certain embodiments, the carrier fluid is selected from fluorocarbonated oils. In certain embodiments, the encapsulating fluid is a silicone oil.

In embodiments in which the target fluid is an aqueous fluid, for example, a biological sample or an aqueous reagent, an example of a CLC includes one in which the carrier (first) fluid is Fluorinert FC-40 (fluorocarbonated oil) having a density of approximately 1,900 kg/m$^3$, the second fluid is a phenylmethylpolysiloxane (silicone oil) having a density of approximately 920 kg/m$^3$, and the target fluid (sample) is an aqueous-based solution of biological components with a density of approximately 1000 kg/m$^3$.

In certain embodiments, the volume of the target fluid (sample) in the CLC is from about 10 nanoliters (nL) to about 20 microliters (μL). As such, in certain embodiments, the volume of the sample is about 10 nL, about 20 nL, about 30 nL, about 40 nL, about 50 nL, about 60 nL, about 70 nL, about 80 nL, about 90 nL, about 100 nL, about 200 nL, about 300 nL, about 400 nL, about 500 nL, about 600 nL, about 700 nL, about 800 nL, about 900 nL, 1 μL, about 2 μL, about 3 μL, about 4 μL, about 5 μL, about 6 μL, about 7 μL, about 8 μL, about 9 μL, about 10 μL, about 11 μL, about 12 μL, about 13 μL, about 14 μL, about 15 μL, about 16 μL, about 17 μL, about 18 μL, about 19 μL, or about 20 μL.

The volume of the carrier and encapsulating fluid in a CLC should be sufficient to generate a composition in which the target fluid can be fully encapsulated between these fluids when present in a desired self-contained CLC location. By fully encapsulated is meant that the target fluid is in direct contact with only the encapsulating fluid and/or the carrier fluid. Thus, the target fluid is not in contact with either the bottom of the self-contained CLC location (generally below the carrier fluid) or to the ambient environment (generally above the encapsulating fluid). The amount of fluid is thus dependent not only on the volume of the target fluid, but also on the interior dimensions of the self-contained CLC location. While the volume of carrier and encapsulating fluid can vary greatly, in certain embodiments, the volume of the carrier fluid or the encapsulating fluid in the CLC is from about 1 μL to about 100 μL. As such, in certain embodiments, the volume of the carrier fluid or the encapsulating is about 1 μL, about 2 μL, about 3 μL, about 4 μL, about 5 μL, about 6 μL, about 7 μL, about 8 μL, about 9 μL, about 10 μL, about 11 μL, about 12 μL, about 13 μL, about 14 μL, about 15 μL, about 16 μL, about 17 μL, about 18 μL, about 19 μL, about 20 μL, about 25 μL, about 30 μL, about 35 μL, about 40 μL, about 45 μL, about 50 μL, about 55 μL, about 60 μL, about 65 μL, about 70 μL, about 75 μL, about 80 μL, about 85 μL, about 90 μL, about 95 μL, or about 100 μL.

An aspect of the thermal chip modules is that they are thermally controlled, such that the temperature of the environment defined by each self-contained CLC location (and therefore experienced by a CLC accommodated therein) may be controlled, e.g., including precisely controlled, e.g., to a tenth of degree or better. The range of temperature control may vary, where in some instances the temperature may be controlled between 4 to 120° C., such as 4 to 98° C. To provide for thermal control, the thermal chip module may include heating and/or cooling elements. In some embodiments, the heating element is integral to the self-contained CLC locations, whereas in other embodiments the heating element and the element defining the self-contained CLC locations are separate, e.g., as a thermal tray and a self-contained CLC locations plate.

The thermal chip module may include a cooling region configured to be operably attached to temperature modulator, e.g., a thermoelectric module, a fluidic cooling system or a forced convection cooling system. The heating element could be, for example, an etched foil heater electrically connected to a controller, the controller being programmed to activate the heating element to generate a desired thermocycle in self-contained CLC locations and the CLCs accommodated therein. The heating element can be incorporated into the self-contained CLC location-defining portion of the thermal chip module or can be provided as a separate element of the module, e.g., as desired.

The thermal chip module is configured to allow for interrogation of each self-contained CLC location by an interrogation station (described in further detail below). In certain embodiments, the interrogation station employs an optical detection system configured to detect an optical emission from the self-contained CLC locations, including but not limited to fluorescence, absorbance, Raman, interferometry and shadow-graphy.

The thermal chip module can also be operatively coupled to a lid sized and shaped to mate with the module or portion thereof so as to enclose the self-contained CLC locations and any CLCs accommodated therein. The lid may be openable and closeable by an automatic actuator (e.g., pneumatically actuated), or may be manually operated. The lid can partially or completely seal to be substantially airtight and/or liquid proof, maintaining a pressure seal. The lid can be transparent to any particularly desired wavelength of light, to allow for interrogation of the CLCs. A heating element can be included in the lid, as desired. The lid can be thermally controlled as desired, such that the temperature of the lid may be modulated to a desired value.

CLC Production Station/CLC Reset Station

The CLC production station is responsible for filling and refilling each self-contained CLC location in the thermal chip module with carrier fluid and encapsulating fluid to create a CLC. An example of a CLC production station is shown in FIGS. 1, 2, 3 and 4 as element D and in FIGS. 14 and 15 as element 24. The CLC production station can include one or more dosage pumps and manifolds (e.g., two, three or more) that allow all the self-contained CLC locations to be addressed. The delivery and heights of each fluid are set by the CLC production station. The CLC production station can also be configured to perform wash processes for the self-contained CLC locations (also referred to as "resetting" the self-contained CLC locations). Cleaning and resetting the self-contained CLC locations can be done by the CLC production/reset station by removing the fluid contents of a self-contained CLC location, e.g., using a vacuum based system, washing the self-contained CLC location, e.g., with one or more ash solutions, and depositing carrier and encapsulating fluids into the self-contained CLC location using the reset and production functions. It is noted that the vacuum and cleaning operations may be performed at a separate location from the CLC deposition operations in the device and using separate deposition heads (see, e.g., element (23) in FIGS. 14 and 15).

The CLC production station can include a carrier-liquid input, an encapsulating-liquid input, a liquid-handling system, and a controller operably connected to the liquid-handling system. The controller can be programmed to cause the liquid handling system to (1) draw a carrier fluid and an encapsulating fluid from the carrier fluid and encapsulating-fluid input, (2) discharge the drawn fluids into a self-contained CLC location of a thermal chip module, the encapsulating fluid being immiscible with the carrier fluid, so that the discharged encapsulating fluid does not mix with the carrier fluid, but instead floats on top of the carrier fluid.

In certain embodiments, the CLC production station includes a reset head (included in element (D) of FIGS. 1, 2, 3 and 4), where the reset head is used to perform CLC deposition and wash processes. A gantry unit can be used to achieve movement in any desired direction to achieve access the required locations within the device, e.g., to the self-contained CLC locations and wash troughs. Mounted into a housing on the gantry, is an aluminum plate (reset plate) onto the underside of which are tip guides. These guides allow two lengths of tubing to be aligned and address self-contained CLC locations on the thermal tray. There are two tiers above the reset plate. Mounted to the upper tier are the pumps and manifolds to the lower.

Figure 2:
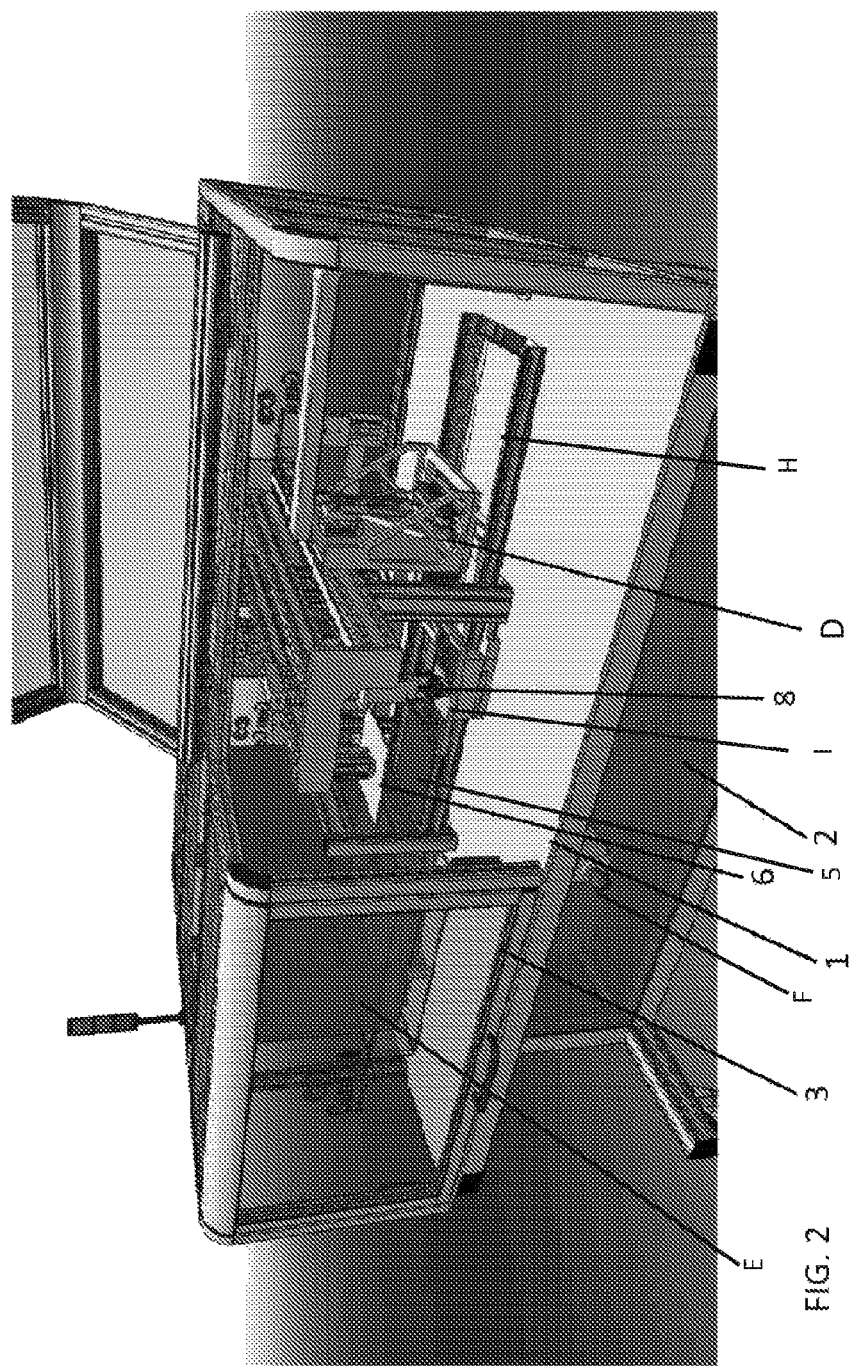
Figure 4:
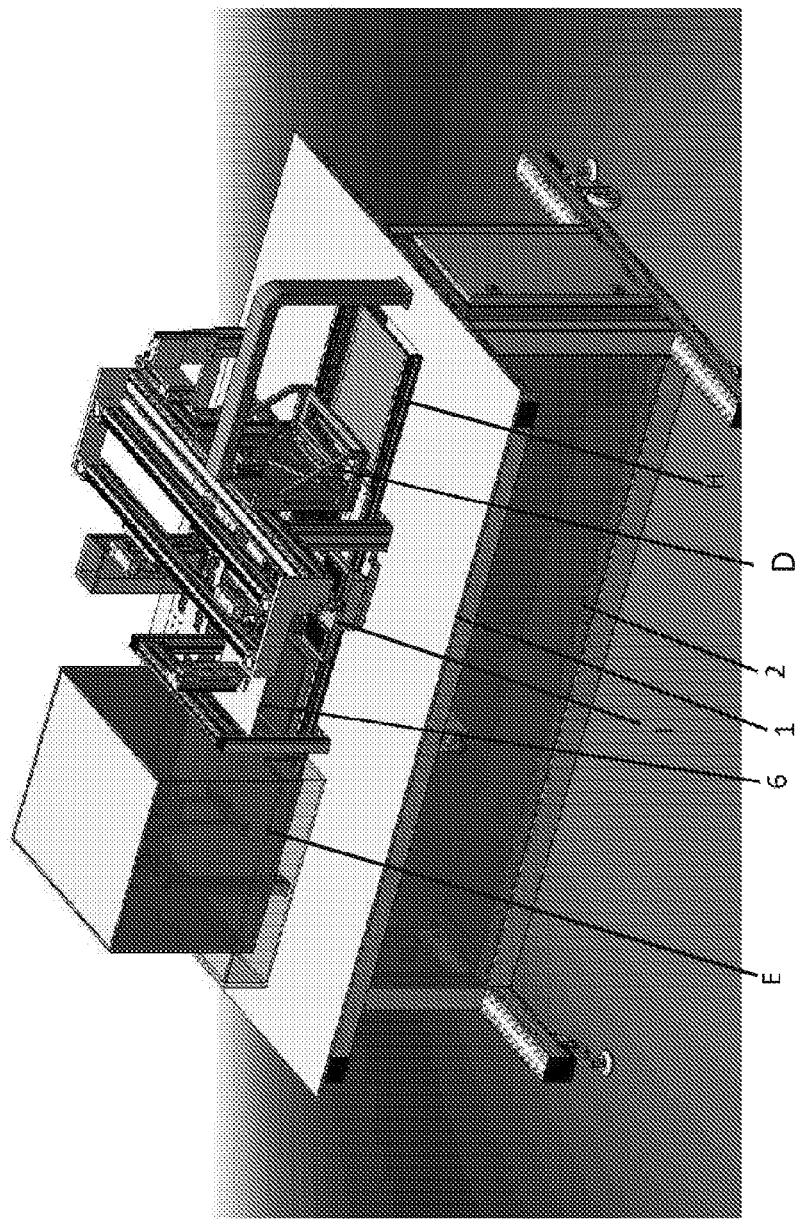
Figure 5:
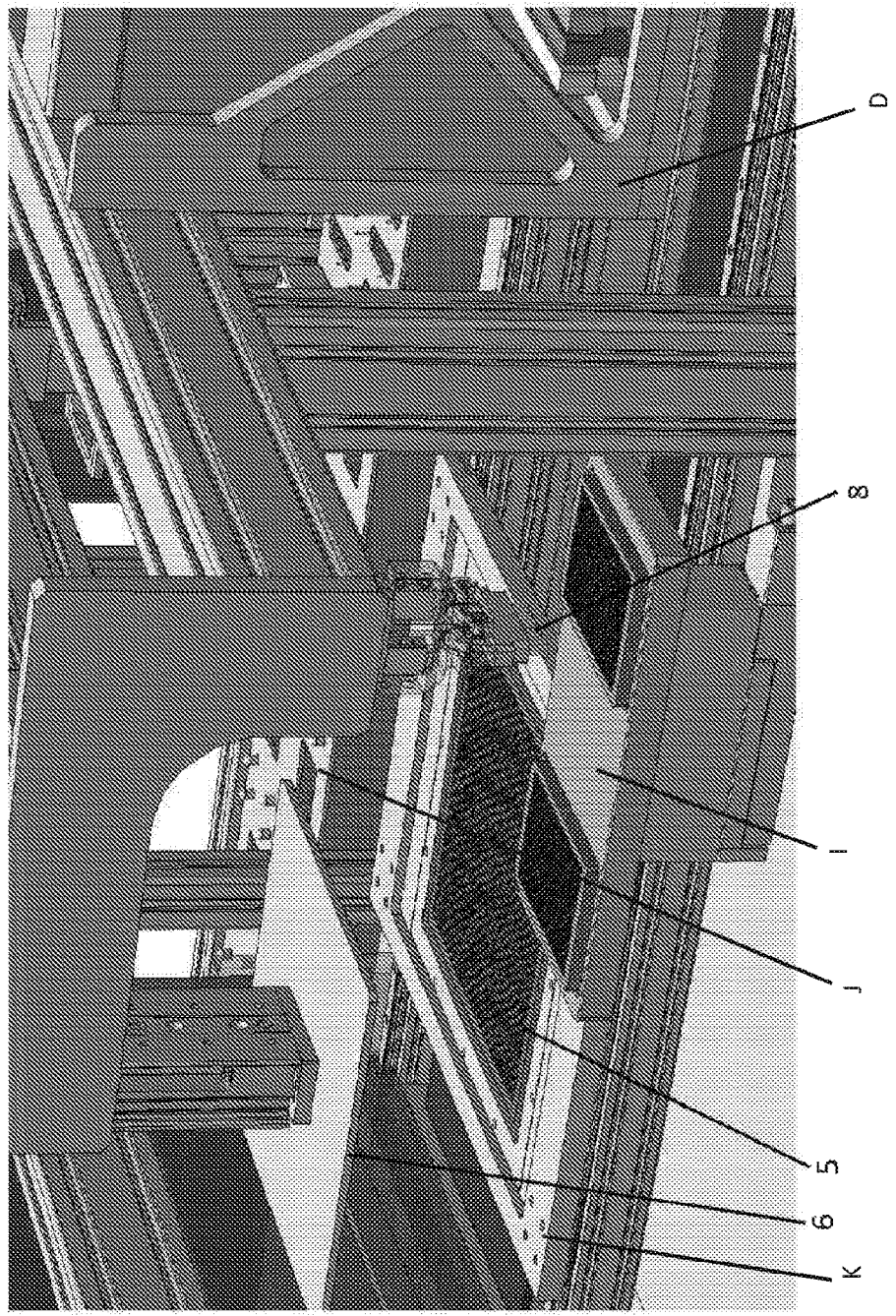

Sample Receiving Location, Reagent Receiving Location, and Plate Locations and Loading Compatibility Sample Receiving Location The sample receiving location is configured to receive biological samples from a desired source in a desired format. In certain embodiments, the sample receiving location accommodates multiplex sample storage systems, e.g., multiwell plates, whereas in other embodiments, the sample receiving location is configured to receive samples from an external sample collection module, e.g., an avian egg sampling unit (ESU) as described below. An example of a sample receiving location is shown in FIGS. 2, 4 and 5 as element (I).

Reagent Receiving Location

The reagent receiving location is configured to receive assay reagents and master mix reagents in and desired format. By assay reagents is meant reagents that are specific to a particular genetic assay (e.g., sequence specific primers, adapters, etc.). By master mix reagents is meant reagents that can be used in multiple different assays (e.g., enzymes, buffers, universal primers, etc.). In certain embodiments, the assay and/or master mix reagents are provided as bulk solutions, e.g., in reagent baths, whereas in other embodiments they are provided in industry standard plates (e.g., 96 well, 384 well, etc.). The reagent receiving location can be configured to receive one or multiple assay reagents and/or one or more master mix reagents at a time.

Plate Locations and Loading Compatibility

As summarized above, devices described herein include one or more plate locations (e.g., for sample plates, assay plates, and master mix plates). While the number of plate locations present in the device may vary, in some instances the device includes 1 to 100 plate locations, such as 10 to 80 plate locations, e.g., 50 plate locations. The plate location(s) may be arranged in any convenient manner in the device, where in some instances the device includes a plurality of plate locations, the plurality of plate locations are arranged adjacent to each other, e.g., in a portrait format relative to an entry port of the device. Plate locations are regions or areas of the device configured to hold a laboratory plate, such as a multi-well plate, e.g., a 96 or 384 multi-well plate, or analogous structure, e.g., a test tube holder or rack, etc. A given plate location may be a simple stage or support configured to hold a laboratory plate. While the dimensions of the plate locations may vary, in some instances the plate locations will have a planar surface configured to stably associate with a laboratory plate, where the planar surface may have an area ranging from 10 mm to 400 mm, such as 10 mm to 200 mm. The planar surface may have any convenient shape, e.g., circular, rectangular (including square), triangular, oval, etc., as desired. To provide for stable association between a plate location and a research plate, the plate location may include one or more stable association elements, e.g., clips, alignment posts, etc.

In some instances, the plate location may be thermally modulated, by which is meant that the temperature of the plate location may be controllable, e.g., so as to control the temperature of a research plate (and the contents thereof) stably associated with the plate location. Any convenient temperature modulator may be employed to control the temperature of the plate location in a desired manner, where temperature modulators that may be employed include those described above in connection with the thermal chip module.

In some instances, a given plate location may be configured to be agitated, i.e., the plate location is a shaker unit. As such, it may include an agitator (e.g., vibrator or shaker component). While the frequency of the movement of the plate location provided by the agitator component may vary, in some instances that agitator may be configured to move the plate location between first and second positions at a frequency ranging from 1 rpm to 4000 rpm, such as 50 rpm to 2500 rpm, where the distance between the first and second positions may vary, and in some instances ranges from 10 mm to 400 mm, such as 25 mm to 100 mm.

The plates can include a 1D and/or a 2D barcode that can be read by an integrated barcode reader, e.g., a manual barcode scanner operated by a user. The scanner barcode information can be used by the device to store information about samples and/or activate a particular program when prompted by the system software, e.g., for running a specific genetic assay.

In some embodiments, plate locations are color-coded to aid user loading.

An example of a plate location are shown in the FIGS. 2, 4 and 5 as element (I).

Robotically Controlled Liquid Handler

As summarized above, devices described herein include a robotically controlled liquid handler. The robotically controlled liquid handler is a unit that is configured to transfer liquid various locations of the device, such as the plate location(s) and the thermal chip module. In a general sense, the robotic liquid handler may be any liquid handling unit that is capable of transferring a quantity of liquid between two distinct locations of the device, such as a plate location and a self-contained CLC location of a thermal chip module. Robotic liquid handlers of interest are ones that can remove a defined volume of liquid from a first location of the device, such as a well of a laboratory plate, and deposit that volume of liquid at second location of the device, e.g., at a self-contained CLC location of a thermal chip module. While the volume of liquid that the handler is configured to transfer may vary, in some instances the volume ranges from 100 nl to 10 ml, such as 100 nl to 1 ml.

The robotic liquid handler is, in some instances, a capillary system configured for dispensing an aqueous liquid. Such a capillary system can include a capillary tube having an inner surface that defines the capillary, or lumen. The tube can also have an outer surface. The outer surface may be generally cylindrical, including the side, top and bottom. The inner surface can include two regions, a distal metering region and a proximal limiting region. The metering region of the inner surface may be substantially hydrophilic while the limiting region of the inner surface may be substantially hydrophobic. The entire outer surface may also be hydrophobic.

When an end, herein labelled the distal end, of the capillary tube is brought into contact with an aqueous sample, the sample is drawn by capillary action into the lumen. But the capillary action will only work to the extent that the aqueous sample is contained within a hydrophilic, i.e., wettable, section of the lumen. When enough aqueous sample has been drawn into the lumen that the metering region is entirely filled, capillary action will cease to draw in additional sample liquid, because no further wettable surface is available to the aqueous sample. In this way, the capillary action can be exploited to precisely meter a desired quantity of aqueous liquid. For a lumen of constant cross-sectional area, the volume of liquid drawn in by capillary action will be equal to the length of the metering section times the cross-sectional area of the lumen.

In some embodiments, the metering region and limiting region can be constructed as follows. A length of capillary tubing can be coated with, or formed entirely from, a hydrophobic polymer, for example a fluorocarbon polymer such as polytetrafluoroethylene (PTFE). An etching solution is then passed through the interior lumen of the tube, stripping the PTFE coating of fluorine atoms near the surface of the PTFE. Fluorine atoms are typically stripped down to a depth a few Angstroms by this process. The resulting etched PTFE surface is hydrophilic. The tube is then cleaned and cut to length to form a metering region having a desired internal volume. That internally etched, internally hydrophilic section of tubing is then attached to a section of hydrophobic tubing to form the entire capillary tube. In some embodiments polymers, such as polyimide, can be used to form the capillary tube.

In some embodiments, the capillary tube is formed of a glass substrate. Glass is naturally hydrophilic, so where the substrate is glass, instead of, for example, a naturally hydrophobic polymer, no surface treatment is necessary to form the metering region. The outer surface and limiting region may be formed by coating the glass with a hydrophobic material, such as the polymers mentioned above.

One benefit of making the outer surface of the tube, especially the distal end of the tube, hydrophobic is that the aqueous sample will not cling to such material. Thus the hydrophobic outer surface protects the system from contaminating one aqueous liquid sample with droplets from a different aqueous sample. Inserting the distal end of the tube into an aqueous sample will results in liquid drawn into the hydrophilic metering region, but not clinging to the hydrophobic region.

In addition to a capillary tube, a capillary system can also include a pressure source in fluid communication with the proximal end of the tube. The pressure source can provide positive pressure from any convenient gas, e.g., air. Application of the positive pressure can be used to drive an aqueous sample out of the capillary. The lowest positive air pressure is found at which the aqueous sample is completely driven out of the capillary and thereafter may be accurately and precisely controlled. The positive pressure may be evenly distributed when there are multiple capillaries used in parallel. The shortest time is found for the positive pressure to be applied to the capillary to allow all of the aqueous sample to be driven out and the pressure neutralized immediately to prevent air being blown out through the capillary once the aqueous has been driven out of the capillary. The positive pressure and time applied may then then be used to carry out sample dispense testing where the sample volume accuracy and precision, sample breakup and disturbance to the CLC are investigated. The positive pressure and time are then adjusted to obtain the optimum sample dispense to CLC within these parameters. The system can also include a capillary controller programmed to apply the positive pressure at a desired time so that the aqueous sample is dispensed at a predetermined location. The location could be, for example, a stabilization site for a composite liquid cell, where an aliquot of encapsulating fluid could be ready to receive the aqueous sample. It should be noted that, while positive pressure can be used to drive the aqueous liquid out of the lumen, no negative pressure is needed to draw the liquid into the lumen because the liquid is drawn in by capillary action.

The capillary system can also include an air sheath, which includes an externally applied air flow to the capillary tube. The externally applied air flow reduces the likelihood that an aqueous sample will attach to any external hydrophilic region.

The capillary system can also include an actuator to move the capillary tube between locations. The actuator can be controlled by the capillary controller, which can be programmed to cause the actuator to move the tube. A typical program might first move the distal end of the tube into contact with an aqueous sample so as to draw the aqueous sample into the tube, then move the capillary tube so that the distal end is adjacent to a dispensing location such as a stabilizing feature or an existing composite liquid cell (hereinafter "CLC"), and finally apply sufficient positive pressure to the proximal end of the tube to eject the aqueous sample from the distal end of the tube.

While the dimensions of the capillary tube may vary, in one embodiment, the internal diameter of the capillary tube is about 200 to 250 µm, such as 221 or 230 µm, and the outer diameter is about 800 µm. Any volume of aqueous solution can be chosen to be drawn into the system. Particular capillary tubes may be designed to draw in from about 10 nanoliters to about 10000 nanoliters, such as 500 nanoliters.

In another embodiment, for multiple capillary metering from a single controller—multiple capillary tubes with the inner surface having a single distal metering region are arranged within a cavity, thereby providing a limiting region.

In another embodiment the pressure controller variably controls the capillary metering volume. The treated tube is cut to a given length and based on the radius of that tube this then gives a set maximum volume. The volume within distal metering region is controlled using air pressure within the assembly. The air pressure is used to dispense however in this embodiment a controlled constant pressure is maintained within the capillary tube—thereby providing a volume control within the hydrophilic distal metering region. This is achieved by balancing the pressure force against the capillary force for a given volume. The fluid will capillary to a height that is matched by pressure force. Change the pressure and the volume is changed. This is all within the total capillary height for a given fluid and tube radius.

In another embodiment, a capillary metering system can include a plurality of capillary tubes. The proximal ends of all the capillaries can be in fluid communication with a single pressure conduit, and the pressure conduit in fluid communication with the pressure source. In this way, a single pressure source can be used to apply a single positive pressure to simultaneously dispense liquid from all of the plurality of capillary tubes. Similarly, a single pressure source can apply a single positive pressure to balance the capillary force in all of the plurality of capillary tubes. In such embodiments, the plurality of capillary tubes may be present in a head subunit which includes a holder for the plurality of capillary tubes. The number of capillary tubes in a head subunit may vary, where in some instances the number ranges from 12 to 768, such as 24 to 384, e.g., 24 to 96, including 24 to 48. The capillary tubes may be arranged in the head subunit so that tubes readily align with wells of a laboratory plate when the head is positioned over a laboratory plate, e.g., one that is present on a plate location of the device. For example, the capillary tubes can be in a 4×32 arrangement that aligns with a 384 well plate, a 2×12 arrangement that aligns with a 96, or other convenient arrangement.

Figure 7:
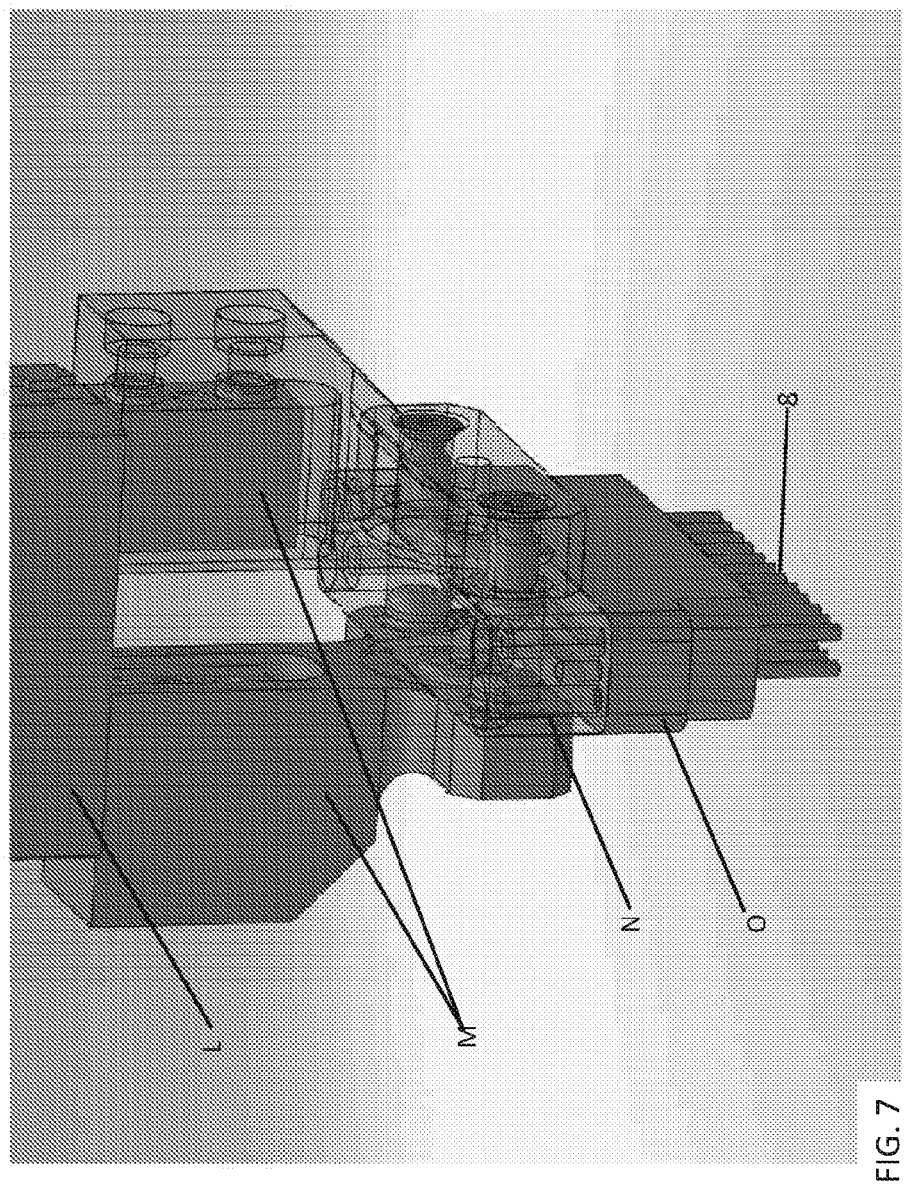
FIG. 7 shows an example of a sample pressure dispensing head according to aspects of the present disclosure.

An example of a sample pressure dispensing head is shown in FIG. 7, which includes a sample head (O) having sample head dispensers (8). The head is engaged with the robotically controlled liquid handler of the device via the sample head lid (N) through a sample gripper (L) having sample gripper arms (M).

Further details regarding capillary liquid handling systems that may be employed in the device are provided in PCT application Serial No. PCT/IB2013/003145 published as WO 2014/08345; the disclosure of which is herein incorporated by reference.

In some instances, the robotic liquid handler includes a mover that can be selectively operatively coupled to a plurality of distinct interchangeable liquid manipulator heads, e.g., capillary heads such as described above. In such embodiments, the mover can be coupled and decoupled to a liquid manipulator head from a collection of two or more liquid manipulator heads, such that the liquid manipulator heads are interchangeable (i.e., can be substituted for one another) with the mover. Where mover provides for negative pressure to the liquid manipulator head when in use, the coupling configuration provides for negative pressure to be coupled to the liquid manipulators, e.g., capillaries, of the head when coupled to the mover. The number of interchangeable liquid manipulator heads in the device may vary, ranging in some instances from 2 to 20, such as 5 to 10. The function of such interchangeable liquid manipulator heads may also vary, where in some instances the device includes interchangeable liquid manipulator heads configured for sample dispense, assay dispense, master mix dispense, and vacuum tasks. The mover to which the interchangeable heads may be operatively coupled is a subunit of the device that is configured to move an interchangeable head between two or more locations of the device. The mover may be a robotic arm or other convenient structure that is configured to move a given interchangeable head in the X and/or Y and/or Z direction in the device.

Interrogation Station

The interrogation station is configured to interrogate each self-contained CLC location of the thermal chip module and obtain a reading therefrom. The reading can be used to determine a genetic characteristic of the sample in the self-contained CLC location after completion of a desired genetic assay protocol, e.g., using the assay and master mix reagents. In FIG. 1, an example of an interrogation station is shown as element (9), while in FIGS. 2, 3, and 4, a specific embodiment of an interrogation station is shown as element (E) (i.e., an optical detection station as described below).

In certain embodiments, the interrogation station is configured to detect an optical signal from each of the self-contained CLC locations. In certain of these embodiments, the optical detections system is configured to transmit excitation light to and collect emission light from each self-contained CLC location in the thermal chip module, where in some instances the emitted light is detected by a camera element of the interrogation station (i.e., the interrogation station comprises a camera-based detection system). Any convenient light can be transmitted by the interrogation station using any convenient light source, e.g., excitation light from a light emitting diode (LED). In some instances, the interrogation station detects multiple wavelengths of light.

Where the interrogation station is configured to detect light (also called an optical detection station), it may include one or more of the following components: one or more light detectors (e.g., a camera), an LED illumination source, a filter or filter wheel containing 2 or more filters (e.g., 3 filters), and one or more optical fibers for light transmission, e.g., 48 individual optical fibers. The optical fibers can be multimodal, meaning that they can transmit excitation light to the self-contained CLC locations and collect the resulting emission light back to the camera based detection system. In some embodiments, a dichroic mirror is used to prevent excitation light from being detected by the camera system. In general, the optical fibers are configured to align with the self-contained CLC locations of the thermal plate module so as to effectively transmit and/or detect light at these locations, and thus the optical fibers can have any convenient spacing to achieve this. In one example, the optical fibers are configured to align with a row of 48 self-contained CLC locations on the thermal chip module and step through each of the 48 rows of self-contained CLC locations. One or more images can be taken on each row, where when multiple images are taken, each one can be at a different wavelength. The system can detect from large droplet sizes down to below 300 nl. The fibers can be mounted into a housing on the gantry on an aluminum plate (or optical plate) onto the underside of which are fiber guides. The fiber guides allow the optical fibers to be aligned and address self-contained CLC locations on the thermal chip module. A single fibre per cluster minimized the need for one fiber per location (for example, 1428 fibers for a thermal chip module having 1428 self-contained CLC locations). The thermal tray is indexed under the fiber to generate the output reading.

The optical unit itself is a contained unit which is mounted on the optical plate. It is here where the samples are optically interrogated via optical fibers which run from the unit through the fiber guides.

Other Components or Subunits

The device can include a Main Deck (element (1) in FIGS. 1, 2 and 4) where all protocol processing steps are performed. User access to the Main Deck can be via a user operated hood that is interlocked. The Services Deck will be mounted under the Main Deck in key-accessible cabinets for troubleshooting and preventative maintenance access.

Figure 3:
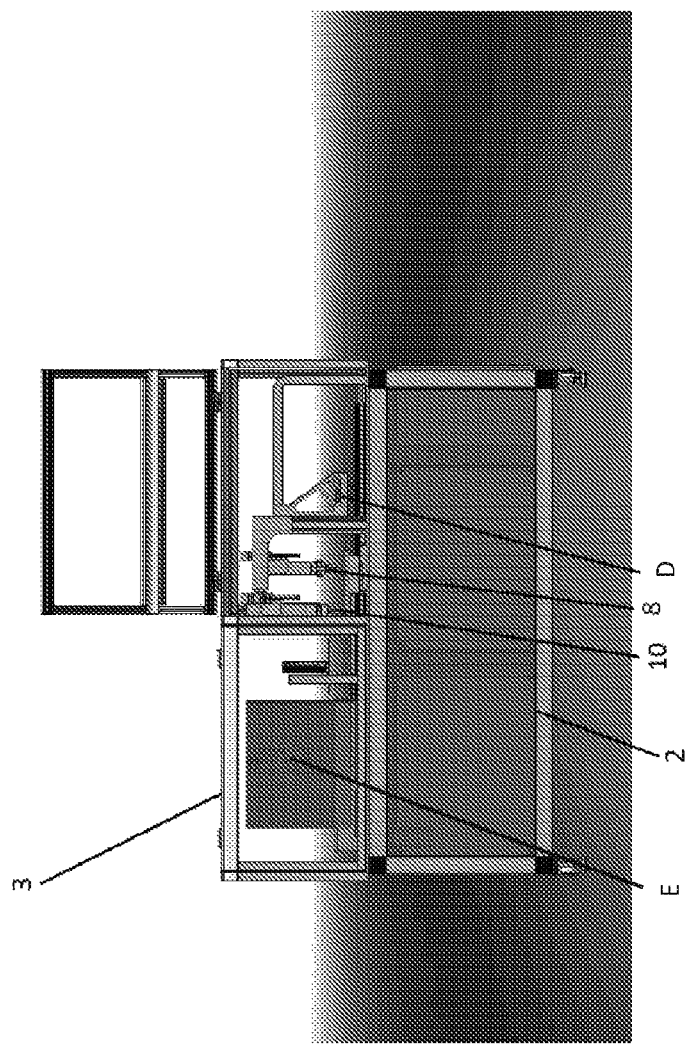

The device can include a Services Deck (element (2) in FIGS. 2, 3, and 4) which can be situated beneath the Main Deck where peripheral hardware is located.

The device can include a System Enclosure (element (3) in FIGS. 1, 2 and 3) that can have active internal-external air exchange and/or thermal control, whereby the enclosure temperature of the system will be managed such that system performance is not affected.

The device can include a Fluidics Module that is located beneath the Main Deck to the system and contains all bottle reservoirs for system fluids and waste collection. The fluidics module can include one or more liquid reservoirs, e.g., for system fluids, waste collection, etc. System fluids of interest include, but are not limited to, encapsulating fluid, carrier fluid, wash fluids, etc. Where desired, the waste collection reservoir is operatively coupled to a single waste drain. Bottles and/or bottle locations can be color coded to aid user loading and avoid error. Bottle reservoirs can have quick-connect connections. Bottles will at minimum contain sufficient volume to complete at least single system run.

The device can include a Barcode Scanner, e.g. a handheld barcode reader, for scanning plates and vessels during run setup and for information tracking.

Figure 9:
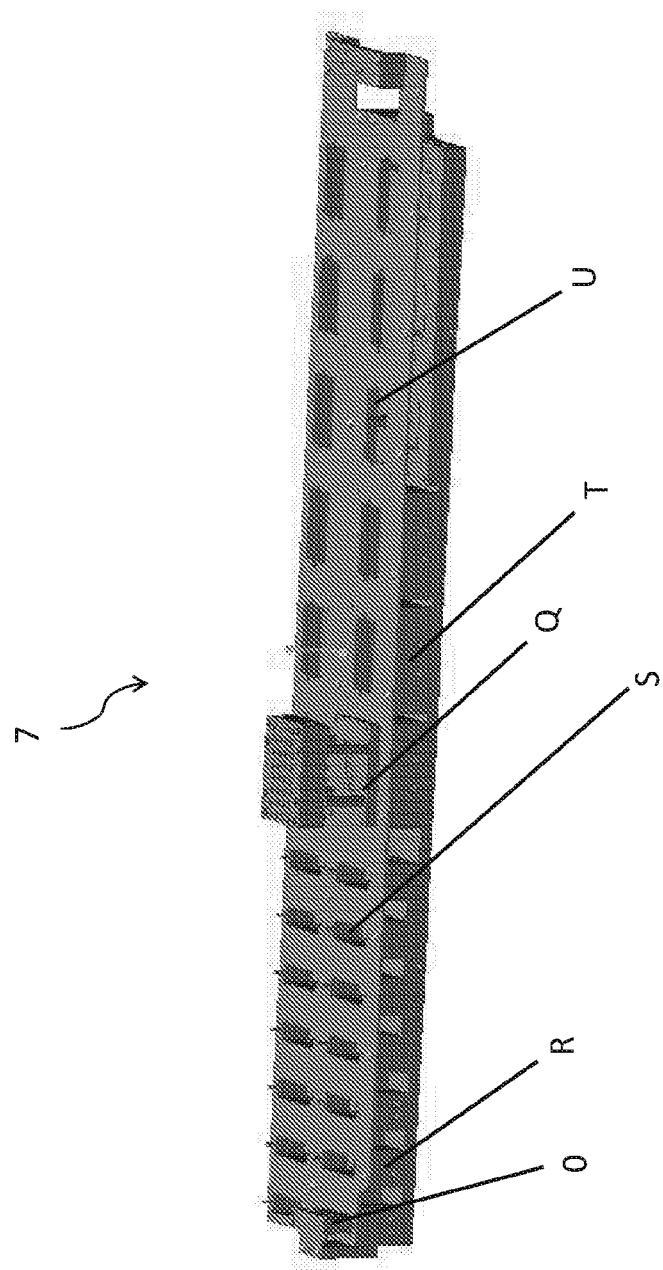
FIG. 9 shows an example of a head cleaning station according to aspects of the present disclosure which is configured for sample and assay head storage, pick-up by the liquid handling system, and to hold assay and sample fluid baths and waste baths.
Figure 10:
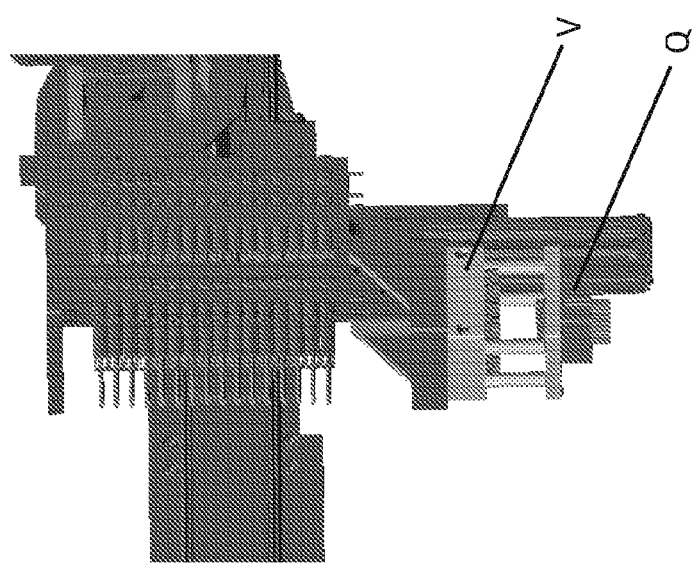
FIG. 10 shows an example of an assay head assembly according to aspects of the present disclosure.

The device can include a Head Cleaning Station to reset each of the pressure dispensing heads. FIG. 9 shows an example of a head cleaning station (7) configured for sample and assay head storage, pick-up by the liquid handling system, and to hold assay and sample fluid baths and waste baths. FIG. 9 shows the placement of a sample head (0) at a first sample fluid bath (a second sample fluid bath is shown as element (R)), a sample waste bath (S), assay head (Q) at a first assay fluid bath (a second assay fluid bath is shown as element (T)), and an assay waste bath (U). FIG. 10 shows an assay head as shown in FIG. 9 (Q) and its corresponding assay head adapter (V) engaged with the robotically controlled liquid handling system when in use to pick up and dispense assay fluids.

The device can include a CLC location Clean-up Station: A similar gantry unit as described above is used to achieve movement in the z direction. Mounted into a housing on the gantry, is an aluminum plate (clean-up plate) onto the underside of which are tip bundle guides. These guides allow bundles of tubing to be aligned and address self-contained CLC locations on the thermal chip module. There are two tiers above the reset plate. Mounted to the upper tier are the pumps and a mixture of 4 line and 8 line manifolds to the lower plate. This station has the ability to use two desired wash solutions. Assigned to each of the solutions are three dosage pumps and three manifolds. The use of manifolds allows all the required self-contained CLC locations to be addressed. Each cluster has two liners and a vacuum line combined together to address the individual self-contained CLC location. To remove liquid from the self-contained CLC locations a vacuum generator is used. The tubing to this generator runs from the tip guides on the plate to a waste bottle.

Operational System Parameters

The system will be compatible with input voltages between 120 and 240 V, input currents of 10-35 amps, and input power frequencies between 50 and 60 Hz. In some applications, the system is to be supplied with dry air at a minimum pressure of 6 bar (87 psi) at a consumption rate of 6 SCFM. In general, Assay and Master Mix reagents will be pre-prepared or otherwise obtained by a user and loaded into barcoded reagent plates (e.g., 'reagent 384 plate') which is subsequently loaded at the reagent location. Further, system fluids will generally be pre-prepared or otherwise obtained by the user and loaded into the Fluidics module.

Specific Embodiments

FIG. 1 shows an example of a device according to aspects of the present disclosure. Features of the device indicated in this figure include the following, each of which is described in detail elsewhere herein: a Main Deck (1), a System Enclosure (3), a Mechanically Actuated Lid for the Thermal Chip Module (6), a Sample Dispensing Head (8), an Interrogation Station (9), an Assay Dispensing Head (10), an AC Power Cabinet (A; an enclosure that houses the power supply units (PSU's) and manages all power coming to the instrument and the power being distributed to the instrument), a Pneumatics Cabinet (B; includes a bank of valves and vacuum generators used for various applications on the instrument), a Fluidic Pumping Cabinet (C; where the fluidics module can house the reservoir bottles which supply system fluids), and a CLC Production and Reset Station (D).

FIG. 2 shows an example of a device according to aspects of the present disclosure. Features of the device indicated in this figure include the following, each of which is described in detail elsewhere herein: a Main Deck (1), a Services Deck (2), a System Enclosure (3), a Thermal Chip Module (5), a Mechanically Actuated Lid for the Thermal Chip Module (6), a Pressure Dispensing Head (8), a CLC Production and Reset Station (D), an Optics Station (E), an E-Stop (F; for emergency shut-down of the device), a Main Rail (H; which allows movement of the thermal chip module between stations in the device), and a Wellplate Holder (I).

FIG. 3 shows an example of a device according to aspects of the present disclosure. Features of the device indicated in this figure include the following, each of which is described in detail elsewhere herein: a Services Deck (2), a System Enclosure (3), a Sample Dispensing Head (8), an Assay Dispensing Head (10), a CLC Production and Reset Station (D), and an Optics Station (E).

FIG. 4 shows an example of a device according to aspects of the present disclosure. Features of the device indicated in this figure include the following, each of which is described in detail elsewhere herein: a Main Deck (1), a Services Deck (2), a Mechanically Actuated Lid for the Thermal Chip Module (6), a CLC Production and Reset Station (D), an Optics Station (E), a Main Rail (H), and a Wellplate Holder (I).

FIG. 5 shows a close-up view of an example of a device according to aspects of the present disclosure. Features of the device indicated in this figure include the following, each of which is described in detail elsewhere herein: a Thermal Chip Module (5), a Mechanically Actuated Lid for the Thermal Chip Module (6), a Sample Dispensing Head (8), a CLC Production and Reset Station (D), a Wellplate Holder (I), a Cleaning Station (J), and a Chip Holder (K).

Figure 6:
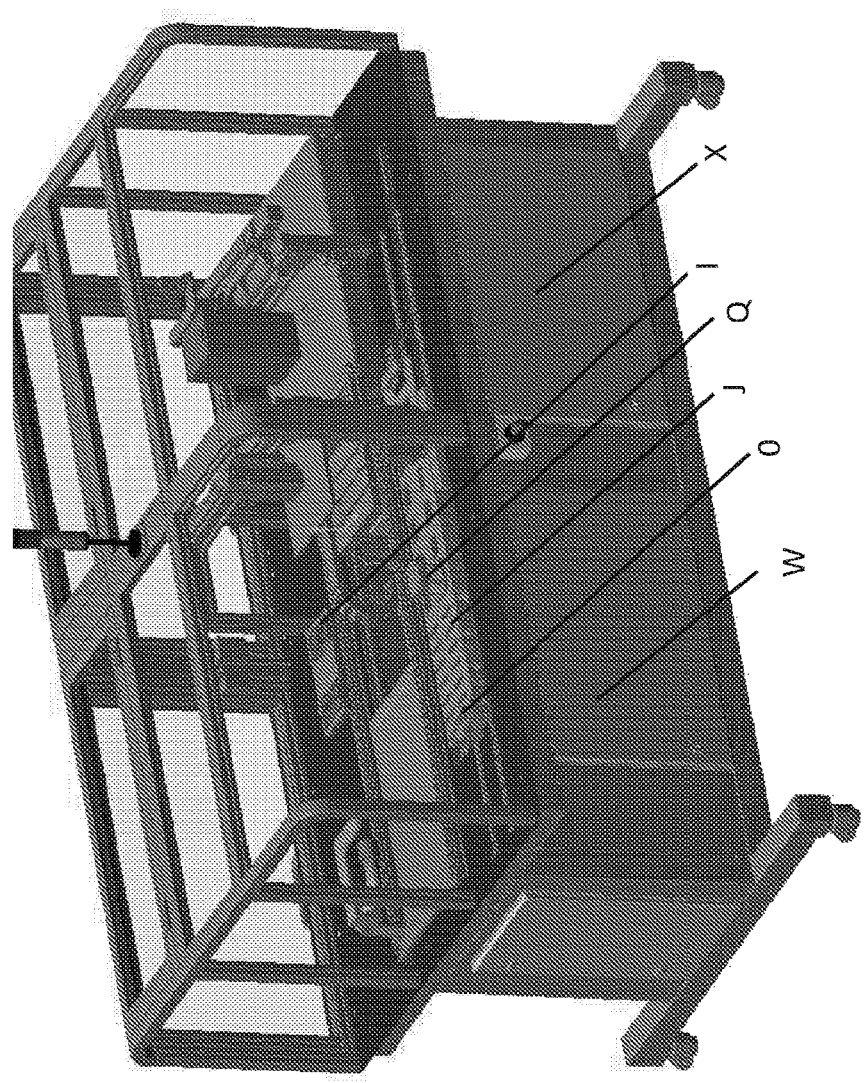

FIG. 6 shows an example of a device according to aspects of the present disclosure. Features of the device indicated in this figure include the following, each of which is described in detail elsewhere herein: a Wellplate Holder (I), a Cleaning Station (J), a Sample Head (0), an Assay Head (Q), a Controller Cabinet (W), and a DC Cabinet (X).

Examples of Genotyping Assays

At a high level, a system for performing a genotyping assay has the following capabilities:

(1) creates individual CLC's on a single chip by prefilling self-contained CLC locations (e.g., a 2304 location chip) with carrier and encapsulating fluids;

(2) creates unique genotyping reactions (e.g., 2304) by the addition of a biological sample;

(3) adds reagents (or a series of reagents) to the self-contained CLC locations and regulates the temperature of the thermal chip module as required to performing the genotyping assay of interest (e.g., primers, buffers, enzymes, detectably-labeled components, etc.); and (4) interrogates the CLC locations to obtain a result for each sample, whereby the genotype of the sample is determined.

It is noted that more than one assay can be performed at a time given the high throughput mature of the device, e.g., 10 different genotyping assays on 384 different samples. The CLCs generated can have low reaction volumes, e.g., on the order of 300 nl, as described above, which can significantly reduce reagent and sample consumption.

The genotyping results can be acquired from the in about 3 hours using Composite Liquid Cells. The device can operate with a minimum sample census of 12 samples and a minimum assay census of 1 assay. For lower numbers samples, an assay can be repeated in each head to ensure the efficient operation of the system.

Genotyping assays that find use in conjunction with the disclosed devices include those based on molecular beacons, FLAP endonucleases (FENS), primer extension reactions, PCR, etc.

Genotyping assays that can be performed include, but are not limited to, the following (each of which are hereby incorporated by reference herein): assays for detecting pathogens (e.g., U.S. Pat. No. 5,968,732 A entitled "Isothermal transcription based assay for the detection and genotyping of dengue virus"; U.S. Pat. No. 8,008,045 B2 entitled "Primers for isothermal amplification of hepatitis C virus") and for determination of a subject's genotype (e.g., PCT Patent Application Publication No. WO 2010054589 A1 entitled "Detection of hla genotype"; PCT Patent Application Publication No. WO 2012006542 A2 entitled "Method of detecting single nucleotide polymorphisms")

Example of Avian Sexing Assay

Molecular sexing of avian eggs is an attractive way to determine the sex of avian subjects. Unlike mammals with XY heterogamety, birds possess a sex chromosomal system with ZW heterogamety in females. More specifically, chromosome W is the female-specific sex chromosome in avian species. Given the ZW heterogamety, chromosome W-specific sequences can be employed to determine the sex of an avian egg using a sample derived therefrom. Polymerase chain reaction (PCR) based approaches that have broad taxonomic utility have been developed. For example, sex identification methods have been based upon examining differences in intron size between the female-specific W chromosome and the Z chromosome, which occurs in both sexes (female, ZW; male, ZZ). For example, Griffiths et al. ((1998), Mol. Evolution. 7:1071-1075) employ PCR with a single set of primers in order to amplify homologous sections of the Z and W gametolog, thereby incorporating introns whose lengths usually differ. Fridolfsson and Ellegren (1999, J. Avian Biol. 30:116-121) developed a similar approach and made use of a combination of the analysis of intron size difference between sexes and the chromosome specific CHD1 gene. Specifically, Fridolfsson and Ellegren developed an allegedly universal method for molecular sexing of non-ratite birds by applying highly conserved primers flanking intron 9 of the CHD1 Wand CHD1Z gene, thereby making use of a constant size difference between CHD1 W and CHD1Z introns. Female birds are thus characterized by displaying one small (CHD1 W) or two fragments (CHD1 W and CHD1Z), while males only show one large fragment CHD1Z). With one particular pair of primers, Fridolfsson and Ellegren were able to sex 47 out of 50 bird species from 11 orders throughout the avian phylogeny.

Examples of genomic assays for avian sex determination that can be performed in the devices include, but are not limited to, those referenced above as well as those described in the following (each of which are hereby incorporated by reference herein in their entirety):

US Patent Application Publication No. US 20120288856 A1 entitled "Molecular sexing of avian subjects"; US Patent Application Publication No. US 20120084873 A1 entitled "Sex-determination and methods of specifying same"; PCT Patent Application Publication No. WO 2004016812 A1 entitled "Avian sex determination method"; PCT Patent Application Publication No. WO 1996039505 A1 entitled "Avian ghd genes and their use in methods for sex identification in birds"; PCT Patent Application Publication No. WO 2014021715 entitled "Gender, viability and/or developmental stage determination of avian embryos in ovo"; Jensen, T et al., "Conditions for rapid sex determination in 47 avian species by PCR of genomic DNA from blood, shell-membrane blood vessels, and feathers", Zoo Biology, Volume 22, Issue 6, pages 561-571, 2003.

Many of the assays described above employ an amplification reaction. In many embodiments, an isothermal amplification is used rather than a standard PCR thermal cycling protocol. One example of an isothermal amplification assay is described in U.S. Pat. No. 6,214,587 B1 entitled "Isothermal strand displacement nucleic acid amplification".

In addition to amplification-based assays, non-amplification based isothermal gender determining assays can be used, e.g., as described in PCT Patent Application Publication No. WO 2008093336 A2 entitled "Genome determination assay". The assay described in this publication directly detects non-amplified genomic DNA and relies upon the ability of the base repair enzyme TDG to recognize and cleave an intact T, mismatched with G, solely in double-stranded DNA. TDG restores T/G mismatches to C/G at sites of methyl cytosine deamination. TDG is shown to recognize a short probe hybridized to a target non-amplified genomic DNA sequence, wherein at one point in the sequence of the primer, C is replaced with T to mismatch G in the target sequence, and TDG is able to cleave the T in the T/G correctly. This permits differentiating between two genomes, and specifically between female and male chicken genomes.

Figure 11:
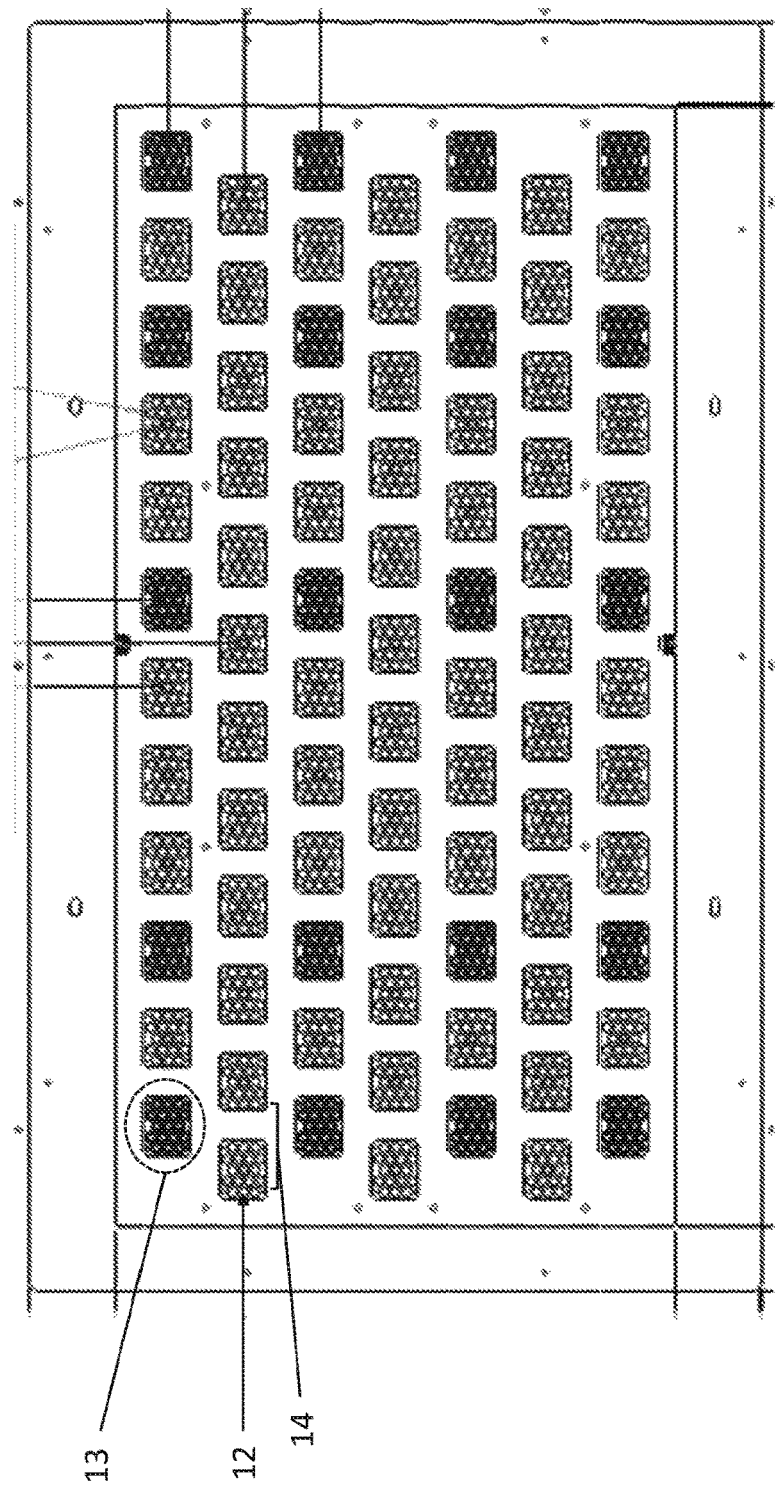
FIG. 11 shows an example of a thermal chip module according to aspects of the present disclosure

In performing an avian gender determination assay, the system capabilities are as follows:

(1) create individual CLCs in the self-contained CLC locations on a thermal chip module (e.g., 84 clusters of 17 self-contained CLC locations for a total of 1428 locations as shown in FIG. 11) by prefilling with oils;

(2) create unique molecular reactions in the CLCs by the addition of a biological sample (e.g., a blood sample) form an avian egg and reagents (or a series of reagents) for performing the sex determination assay;

(3) thermally lyses/processes the biological samples within the self-contained CLC locations to run the genetic avian sex determination assay;

(4) interrogates the CLC locations to obtain a result for each sample, whereby the sex of the avian egg is determined.

In some embodiments, the CLCs generated can have a reaction volume on the order of 10 to 20 ul e.g., 15 uL. The device can operate with a minimum sample census of 20 samples and a minimum assay census of 1 assay. For lower numbers samples, an assay can be repeated in each head to ensure the efficient operation of the system. The system can provide gender calls using an isothermal chemistry results in about 15 minutes using Composite Liquid Cells. The system operates with a two color fluorescent detection system.

As detailed elsewhere herein, the Assay Processing Unit (APU) has the ability to interact with the Egg Sampling Unit (ESU) via a set of extended rails (not included in the overall dimensions of the APU). The combined units together are used to make gender calls on in vitro chicks. The system is designed to be controlled via a user interface on a typical Windows personal computer which is built into the frame of the instrument.

The ESU is the module that harvests the samples (the biological sample from the avian eggs). The APU has the following operations performed within it including; sample dispense; sample lysing; thermal incubation; assay dispense; signal amplification through thermal incubation; optical read; and self-contained CLC location reset.

The Thermal Chip Module can be an aluminum plate enclosure that is mounted on two linear bearings via four carriages which are part of the linear rail assembly. It is a modular unit and can be decoupled from the instrument by connecting/disconnecting the various electrical and pneumatic contacts in the termination zone, located at the back of the module.

Access to the internal components can be gained via five access plates (two on each of the side walls and one on the underside) or by removing the lids of the module.

The thermal tray is housed within the thermal chip module and defines the 1428 self-contained CLC locations. FIG. 11 shows an example of a thermal chip module with self-contained CLC locations (12) in clusters (13) spaced at a pitch (14) for sampling avian eggs. The self-contained CLC locations are present in a thermal tray of the thermal chip module. Each cluster contains 17 self-contained CLC locations for running independent avian sexing assays on different egg-derived biological samples. The thermal tray is independently controlled using a wire wound conductive heater mat bonded to the lower surface of the thermal tray. The cooling of the thermal tray is provided by turbulent air flow ducts located on the under side of the heater mat.

The liners of the self-contained CLC locations can be injected molded black to minimize internal reflections and background signal (this can be applied to any device described herein).

The XY directional movement of the thermal tray is achieved using and XY stage that is permanently contained within the module, onto which the thermal tray mounts. This removes the need for additional robotics within the various heads.

The thermal chip module has the capability of operation within a dusty environment with two lids on the module to prevent the ingress of dust. Both lids have holes corresponding to that of the self-contained CLC locations on the thermal tray. An upper lid fixed to the module while the lower lid is mounted on a mechanism that can be actuated by 10 mm. By actuating the lower lid and offsetting the holes, this ensures the module is closed to the environment and thus prevents any ingress of dirt. Positive pressure is also used to ensure air-flow is always from the tray to ambient.

Figure 12:
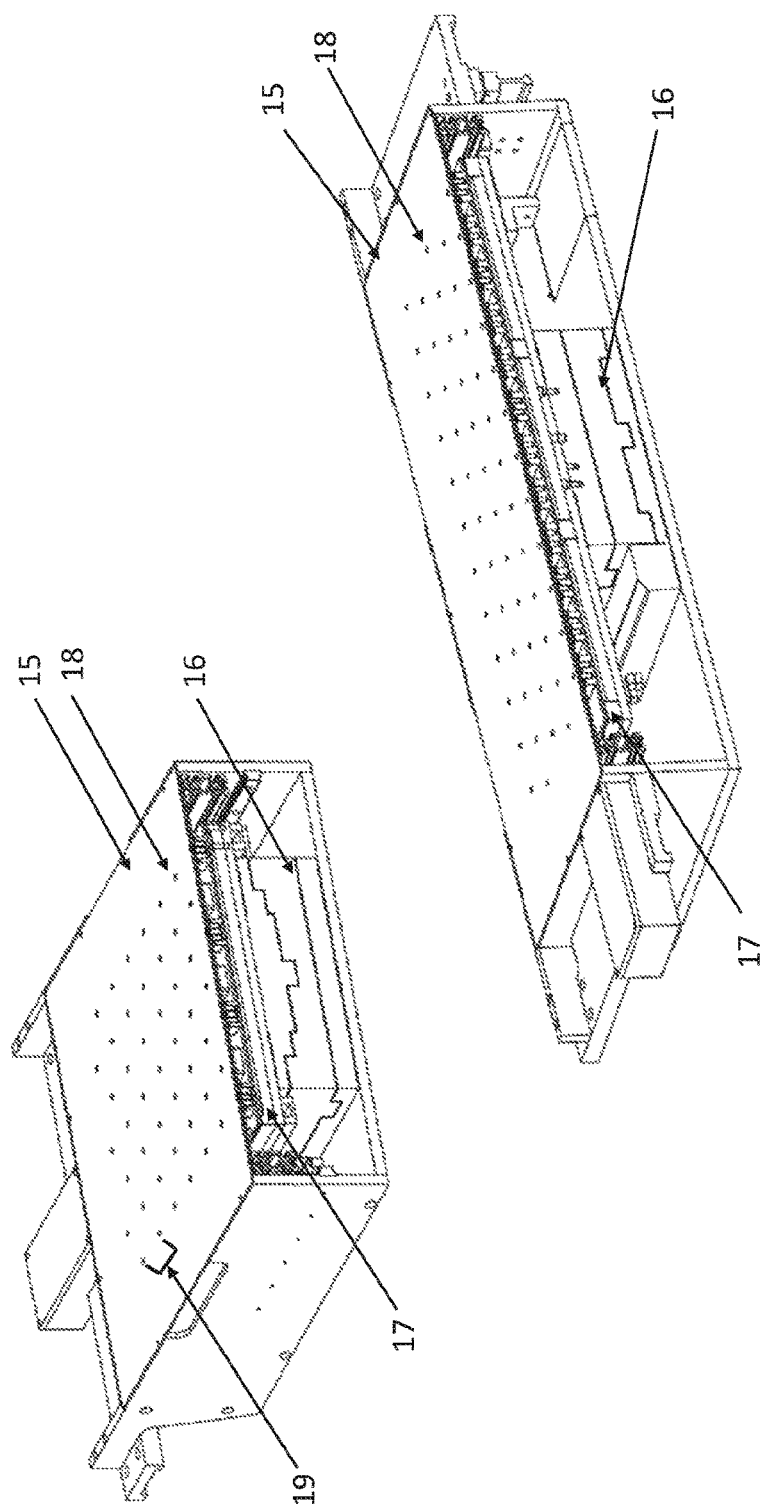
FIG. 12 shows two views of a thermal chip module according to aspects of the present disclosure

FIG. 12 shows two views of a thermal chip module assembled with a module lid (15) having holes (18) corresponding to a single self-contained CLC location in each cluster (shown in FIG. 11) at egg pitch distance (19) mounted on a robotic XY stage (16). The thermal chip module includes an integrated thermal tray base (17) for temperature control.

Figure 13:
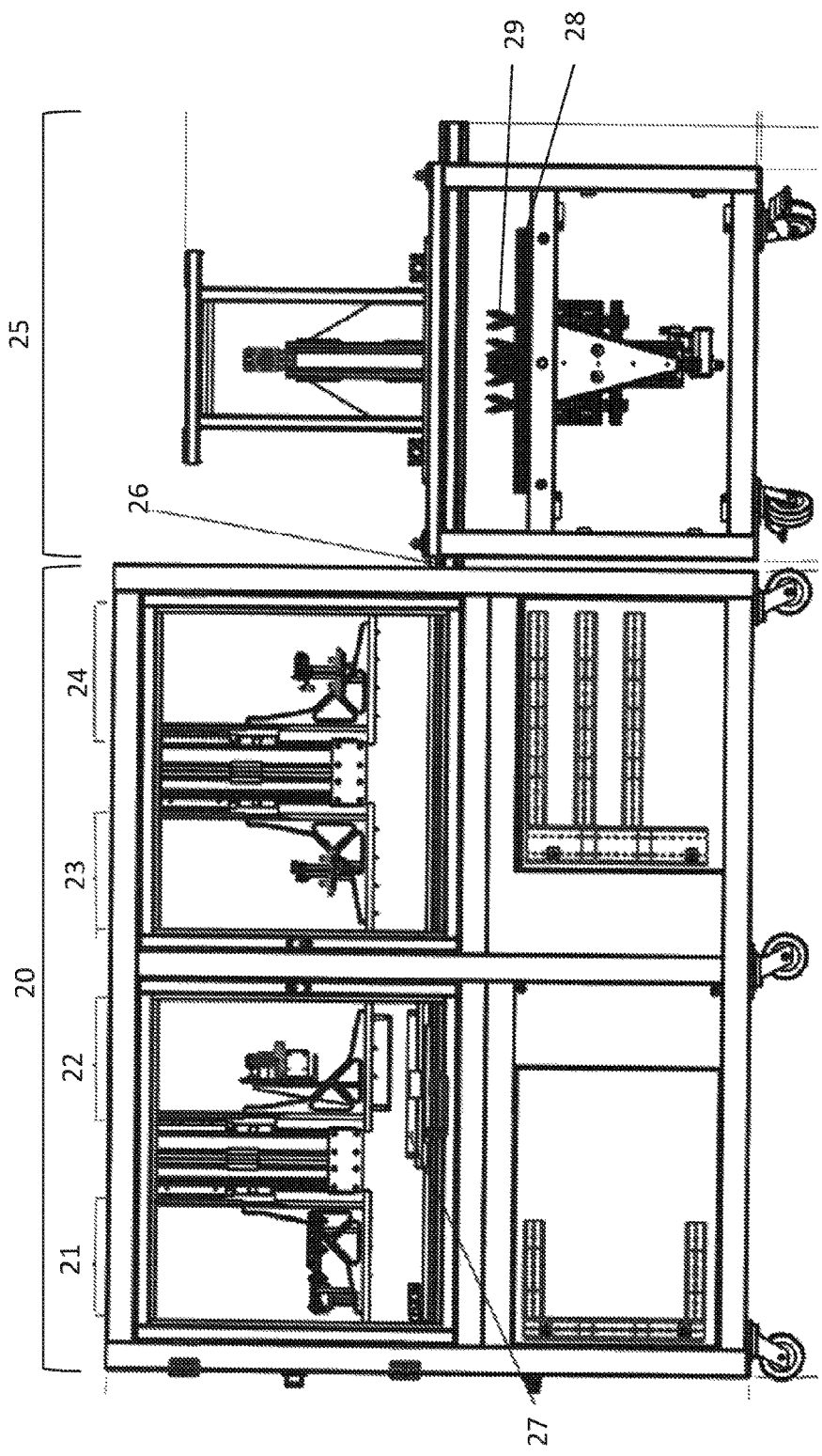
FIG. 13 shows an example of an avian egg sexing device according to aspects of the present disclosure having an Assay Processing Unit (APU; 20) operatively connected to an egg sampling unit (ESU; 25) via a linear rail (26) that permits interaction and movement of the thermal chip module (27) between the APU and the ESU.

FIG. 13 shows an example of an avian egg sexing device that finds use in avian sex determination. The device shown in FIG. 13 has an Assay Processing Unit (APU; 20) containing: an assay dispense station (21) an optical interrogation station (22), a vacuum/head reset station (23), and a CLC production station (24). The APU is operatively connected to an egg sampling unit (ESU; 25) via linear rails (26) that permits interaction and movement of the thermal chip module (27) between the APU and the ESU. The linear rails of the device can be constructed form 80 mm×40 mm extruded aluminum, to which linear bearings are mounted. A linear motor and magnetic track can be used to drive the thermal chip module along the rails. The magnetic track can be located on the inside of the front rail. The motor itself attaches then to the underside of the thermal chip module. Positional feedback from the motor can be performed through the use of a reader head and encoder strip combination. This stainless steel encoder strip can be located on the inside of the back rail. Rollers can also be attached to the inside of the rails. These can be used to accommodate a stainless steel drip tray, the purpose of which is to protect the internal compartments of the instrument during the priming of the pumps. The ESU includes an avian egg tray (28) with a plurality of egg receivers (29) spaced at an egg pitch.

Figure 14:
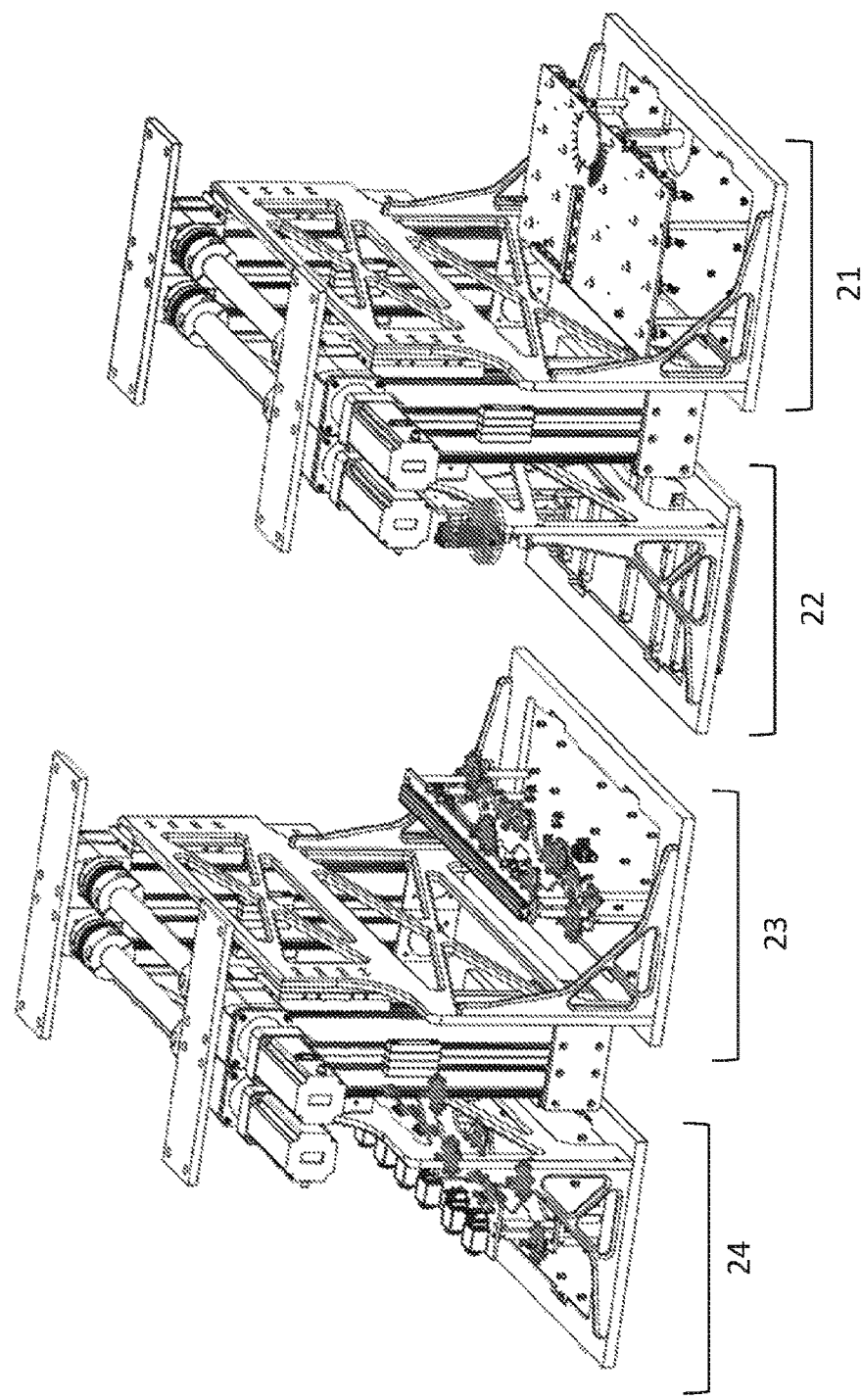
FIG. 14 shows close-up schematics of the assay dispense station (21) optical interrogation station (22), vacuum/head reset station (23), and CLC production station (24) of FIG. 13.

The ESU includes an egg sampling head that includes needles spaced at egg pitch to obtain a biological sample from each egg in the egg tray. The linear rails allow the thermal chip module to be moved to the ESU to receive the biological samples collected by the egg sampling head. Multiple rounds of sample collection and deposition can be performed to deposit different samples all of the self-contained CLC locations in the clusters on the thermal chip module (e.g., the 17 self-contained CLC locations on the thermal chip module shown in FIG. 11). FIG. 14 shows close-up schematics of the assay dispense station (21) optical interrogation station (22), vacuum/head reset station (23), and CLC production station (24) of FIG. 13.

All of the components above can be controlled and supplied by the following 6 units:

(1) AC Power Unit/Cabinet: an enclosure that houses the power supply units (PSU's). It also manages all power coming to the instrument and the power being distributed to the instrument.

(2) A DC Comms Unit/Cabinet: the unit where all the DC power from the PSU's is terminated. It contains multiple termination blocks, relays, digital outputs/inputs and mini8.

(3) A Control Unit/Cabinet: this contains multiple drivers (e.g., seven drivers) that control all robotic movement on the instrument. It is here that all the contacts relating to the safety system are located.

(4) An Air Filter Unit: air is filtered and regulated around the instrument through this unit.

(5) A Pneumatic Station/Cabinet: this includes a bank of valves and vacuum generators used for various applications on the instrument.

(6) Fluidics Module/Fluidics Pumping Cabinet: Below the main deck is where the fluidics module can house the reservoir bottles which supply system fluids; encapsulant oil, carrier oil, wash liquids. Placeholders will be colour coded or numbered to aid user setup and avoid errors. Bottle reservoirs will have quick-connect connections. Bottles will at minimum contain sufficient volume to complete a single system run.

Computer Controllers

Aspects of the present disclosure further include computer controllers for operating the devices, where the controllers further include one or more computer elements for complete automation or partial automation of a device as described herein. In some embodiments, the controllers include a computer having a computer readable storage medium with a computer program stored thereon, where the computer program when loaded on the computer includes instructions for actuation the device to perform a CLC mediated genetic assay, e.g., as described above.

In embodiments, the controller includes an input module, a processing module and an output module. Processing modules of interest may include one or more processors that are configured and automated to implement one or more routines of the device, e.g., as described above. For example processing modules may include two or more processors, such as three or more processors, such as four or more processors and including five or more processors, that are configured and automated to perform a genetic assay. As described above, each processor includes memory having a plurality of instructions for performing the steps of the subject methods.

The controllers may include both hardware and software components, where the hardware components may take the form of one or more platforms, such that the functional elements, i.e., those elements of the controller that carry out specific tasks (such as managing input and output of information, processing information, etc.) of the controller may be carried out by the execution of software applications on and across the one or more computer platforms represented of the system.

Controllers may include a display and operator input device. Operator input devices may, for example, be a keyboard, mouse, or the like. The processing module includes a processor which has access to a memory having instructions stored thereon for performing the steps of the subject methods. The processing module may include an operating system, a graphical user interface (GUI) controller, a system memory, memory storage devices, and input-output controllers, cache memory, a data backup unit, and many other devices. The processor may be a commercially available processor or it may be one of other processors that are or will become available. The processor executes the operating system and the operating system interfaces with firmware and hardware in a well-known manner, and facilitates the processor in coordinating and executing the functions of various computer programs that may be written in a variety of programming languages, such as Java, Perl, C++, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques.

The system memory may be any of a variety of known or future memory storage devices. Examples include any commonly available random access memory (RAM), magnetic medium such as a resident hard disk or tape, an optical medium such as a read and write compact disc, flash memory devices, or other memory storage device. The memory storage device may be any of a variety of known or future devices, including a compact disk drive, a tape drive, a removable hard disk drive, or a diskette drive. Such types of memory storage devices typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with the memory storage device.

In some embodiments, a computer program product is described comprising a computer usable medium having control logic (computer software program, including program code) stored therein. The control logic, when executed by the processor the computer, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Memory may be any suitable device in which the processor can store and retrieve data, such as magnetic, optical, or solid state storage devices (including magnetic or optical disks or tape or RAM, or any other suitable device, either fixed or portable). The processor may include a general purpose digital microprocessor suitably programmed from a computer readable medium carrying necessary program code. Programming can be provided remotely to processor through a communication channel, or previously saved in a computer program product such as memory or some other portable or fixed computer readable storage medium using any of those devices in connection with memory. For example, a magnetic or optical disk may carry the programming, and can be read by a disk writer/reader. Systems of the invention also include programming, e.g., in the form of computer program products, algorithms for use in practicing the methods as described above. Programming according to the present invention can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; portable flash drive; and hybrids of these categories such as magnetic/optical storage media.

The processor may also have access to a communication channel to communicate with a user at a remote location. By remote location is meant the user is not directly in contact with the system and relays input information to an input manager from an external device, such as a computer connected to a Wide Area Network ("WAN"), telephone network, satellite network, or any other suitable communication channel, including a mobile telephone (i.e., smartphone).

In some embodiments, controllers according to the present disclosure may be configured to include a communication interface. In some embodiments, the communication interface includes a receiver and/or transmitter for communicating with a network and/or another device. The communication interface can be configured for wired or wireless communication, including, but not limited to, radio frequency (RF) communication (e.g., Radio-Frequency Identification (RFID), Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM).

Output controllers may include controllers for any of a variety of known display devices for presenting information to a user, whether a human or a machine, whether local or remote. If one of the display devices provides visual information, this information typically may be logically and/or physically organized as an array of picture elements. A graphical user interface (GUI) controller may include any of a variety of known or future software programs for providing graphical input and output interfaces between the system and a user, and for processing user inputs. The functional elements of the computer may communicate with each other via system bus. Some of these communications may be accomplished in alternative embodiments using network or other types of remote communications. The output manager may also provide information generated by the processing module to a user at a remote location, e.g., over the Internet, phone or satellite network, in accordance with known techniques. The presentation of data by the output manager may be implemented in accordance with a variety of known techniques. As some examples, data may include SQL, HTML or XML documents, email or other files, or data in other forms. The data may include Internet URL addresses so that a user may retrieve additional SQL, HTML, XML, or other documents or data from remote sources. The one or more platforms present in the subject systems may be any type of known computer platform or a type to be developed in the future, although they typically will be of a class of computer commonly referred to as servers. However, they may also be a main-frame computer, a work station, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include Windows NT®, Windows XP, Windows 7, Windows 8, iOS, Sun Solaris, Linux, OS/400, Compaq Tru64 Unix, SGI IRIX, Siemens Reliant Unix, and others.

Below are examples of software elements that find use in the present devices and methods:

Input File: The number of samples and assays to be run can be captured during run setup either through manually entered user data or a previously generated .csv file. Information to be captured will include number of samples and location of samples. For inputting run details manually, a blank template can be used with autofill options to populate information quickly for later editing.

Main User Interface: The main user interface will feedback the following run status information: an animated graphical representation of the main deck showing current action being performed by the liquid handler; a status indicator for each chip indicating its progress through the overall protocol; a countdown timer to the completion of the total run, accurate to +/−10 min; a feedback panel for the chip which will show information pertaining to the current task being performed, i.e., thermal information, dispense operation, and optical readings; a warnings and errors panel where any issues flagged by software will be displayed.

Output File: The output files, including a barcoding file, and a plate definition file, can be optionally amalgamated into one. The name of the run log folder will be included in the output file as well as the protocol that was run. Run logs will be numbered to keep them in order.

General Software Requirements: During run setup a user will be guided through the loading sequence and prompted to scan the barcode when appropriate. The system's software will include a specific simple and integrated sub-program for bulk dispensing chip alignment. When a user is required to enter information, is the system can prompt them to select from a number of predefined options within a drop-down list rather than freely entering information.

Some individual elements of the system have been previously described in, for example, U.S. Pat. No. 8,465,707, U.S. Provisional Patent Applications Ser. Nos. 61/590,499, 61/730,336, 61/836,461, 61/908,473, 61/908,479, and 61/908,489, and International Patent Application Ser. Nos. PCT/US2013/023161 and PCT/US2013/071889.

This genotyping system is compatible with molecular chemistries used in high throughput genotyping. These include and are not limited to samples from DNA, RNA, whole exome, transcriptome, virsuses, BAC's, etc.

Additional details regarding systems that may be configured to perform the fluid manipulation methods described herein, and therefore include the fluid handling systems described herein; include those described in U.S. Pat. Nos. 8,465,707 and 9,080,208; as well as United States Patent Application Publication No. 20140371107; and Published PCT Application Nos: WO2014/083435; WO2014/188281; WO2014/207577; WO2015/075563; WO2015/075560; the disclosures of which applications are herein incorporated by reference.

The methods and systems described herein find use in a variety of different applications. Applications in which the methods and systems find use include CLC mediated protocols, including but not limited to those described in U.S. Pat. Nos. 8,465,707 and 9,080,208; as well as United States Patent Application Publication No. 20140371107; and Published PCT Application Nos: WO2014/083435; WO2014/188281; WO2014/207577; WO2015/075563; WO2015/075560; the disclosures of which applications are herein incorporated by reference.

Notwithstanding the appended clauses, the disclosure set forth herein is also defined by the following clauses:

1. A complete genomic analysis device, the device comprising:
  a thermal chip module comprising multiple self-contained composite liquid cell (CLC) locations;
  a CLC production station configured to access each self-contained CLC location of the thermal chip module;
  a sample receiving location;
  a reagent receiving location;

a robotically controlled liquid handler configured to transfer liquid between the sample receiving location, the reagent receiving location, and the thermal chip module; and an interrogation station configured to interrogate each self-contained CLC location of the thermal chip module.

2. The device according to Clause 1, wherein the thermal chip module comprises from 1400 to 3000 self-contained CLC locations.

3. The device according to Clause 1 or 2, wherein the device comprises a mechanically actuated lid for the thermal chip module.

4. The device according to any of Clauses 1 to 3, wherein the reagent receiving location is configured to receive an assay plate and a master mix plate.

5. The device according to Clause 4, wherein the reagent receiving location is configured to receive multiple assay plates.

6. The device according to Clause 4 or 5, wherein the assay and master mix plates are standard laboratory plates.

7. The device according to any of Clauses 1 to 6, wherein the robotically controlled liquid handler comprises interchangeable heads configured for sample dispense, assay dispense, and master mix dispense operations.

8. The device according to any of Clauses 1 to 7, wherein the CLC production station is configured to dispense carrier and encapsulating fluid into the self-contained CLC locations and wash the self-contained CLC locations.

9. The device according to any of Clauses 1 to 8, wherein the device comprises a fluidics module comprising liquid reservoirs for system fluids and waste collection.

10. The device according to any of Clauses 1 to 9, wherein the device is operatively coupled to a barcode scanner.

11. The device according to any of Clauses 1 to 10, wherein the interrogation station is configured to detect an optical signal.

12. The device according to Clause 11, wherein the interrogation station is configured to transmit excitation light to and collect emission light from each self-contained CLC location in the thermal chip module.

13. The device according to Clause 12, wherein the interrogation station comprises a camera based detection system.

14. The device according to Clause 12 or 13, wherein the excitation light is from a LED.

15. The device according to any of Clauses 12 to 14, wherein the interrogation station detects multiple wavelengths of light.

16. The device according to any of Clauses 1 to 15, wherein the device is a genotyping device.

17. The device according to Clause 16, wherein the sample receiving location is configured to receive a sample plate.

18. The device according to Clause 17, wherein the sample plate is a standard laboratory plate.

19. The device according to Clause 17 or 18, wherein the sample receiving location is configured to receive multiple sample plates.

20. The device according to any of Clauses 1 to 15, wherein the device is an avian sexing device.

21. The device according to Clause 20, wherein the sample receiving location is operatively connected to an egg sampling unit (ESU) configured to obtain biological samples from multiple avian eggs.

22. The device according to Clause 21, wherein the self-contained CLC locations of the thermal chip module are arranged in multiple clusters that are spaced at a pitch configured for receiving the biological samples from the multiple avian eggs.

23. The device according to Clause 22, wherein each of the multiple clusters comprises from 2 to 40 self-contained CLC locations.

24. The device according to Clause 23, wherein the thermal chip module comprises 84 clusters each comprising 17 self-contained CLC locations.

25. The device according to any of Clauses 20-24, wherein the thermal chip module comprises an upper lid and a lower lid, wherein the upper lid and lower lid comprise holes corresponding to the self-contained CLC locations, wherein the upper lid is fixed to the thermal chip module such that the holes are aligned with the corresponding self-contained CLC locations and the lower lid is mounted on a mechanism that can be actuated to offset the alignment of the holes with the upper lid to close the holes in the upper lid.

26. A method of genomically analyzing a plurality of biological samples, the method comprising:

introducing a plurality of biological samples into the sample location of a device according to any of Clauses 1 to 24;

operating the device to perform a genotyping assay by:

(i) generating a CLC genomic analysis reaction sample for each of the plurality of biological samples in a corresponding self-contained CLC location of the thermal chip module;

(ii) performing a reaction in the CLC genomic analysis reaction sample by running a thermal program on the thermal chip module; and (iii) detecting a signal from each of the CLC genomic analysis reaction samples in the corresponding self-contained CLC locations of the thermal chip module with the interrogation station;

wherein the signal detected for each of the CLC genomic analysis reaction samples is indicative of a genetic characteristic of each of the plurality of biological samples.

27. The method according to Clause 26, wherein each of the CLC genomic analysis reaction samples is in a total volume of 300 nl.

28. The method according to Clause 26 or 27, further comprising introducing into the device an assay plate comprising a reagent for performing the genotyping assay.

29. The method according to Clause 8, wherein multiple different genomic analysis assays are performed.

30. The method according to Clause 29, wherein a different assay plate is introduced into the device for each of the multiple different genomic analysis assays performed.

31. The method according to any one of Clauses 26 to 30, wherein the generating step comprises:

operating the CLC production station to dispense a carrier fluid and an encapsulating fluid into each self-contained CLC location of the thermal chip module; and operating the robotically controlled liquid handler to:

dispense each of the plurality of biological samples into a corresponding self-contained CLC location of the thermal chip module;

dispense an assay reagent into each self-contained CLC location of the thermal chip module; and dispense a master mix reagent into each self-contained CLC location of the thermal chip module.

32. The method according to any of Clauses 26 to 31, wherein the genomic analysis assay is a genotyping assay.

33. The method according to any of Clauses 26 to 31, wherein the genomic analysis assay is an avian sexing assay.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

We claim:

1. A complete genomic analysis device, the device comprising:
   a thermal chip module comprising multiple self-contained composite liquid cell (CLC) locations;
   a CLC production station configured to access each self-contained CLC location of the thermal chip module;
   a sample receiving location;
   a reagent receiving location;
   a robotically controlled liquid handler configured to transfer liquid between the sample receiving location, the reagent receiving location, and the thermal chip module;
   an interrogation station configured to interrogate each self-contained CLC location of the thermal chip module,
   wherein the thermal chip module, the CLC production station, the sample receiving location, the reagent receiving location, and the interrogation station are positioned on a main deck of the device; and
   an egg sampling unit operatively connected to the sample receiving location and configured to obtain biological samples from multiple avian eggs.

2. The device according to claim 1, wherein the thermal chip module comprises from 1400 to 3000 self-contained CLC locations.

3. The device according to claim 1, wherein the device comprises a mechanically actuated lid for the thermal chip module.

4. The device according to claim 1, wherein the reagent receiving location is configured to receive an assay plate and a master mix plate.

5. The device according to claim 1, wherein the robotically controlled liquid handler comprises interchangeable heads configured for sample dispense, assay dispense, and master mix dispense operations.

6. The device according to claim 1, wherein the CLC production station is configured to dispense carrier and encapsulating fluid into the self-contained CLC locations and wash the self-contained CLC locations.

7. The device according to claim 1, wherein the device comprises a fluidics module comprising liquid reservoirs for system fluids and waste collection.

8. The device according to claim 1, wherein the interrogation station is configured to detect an optical signal.

9. The device according to claim 8, wherein the interrogation station is configured to transmit excitation light to and collect emission light from each self-contained CLC location in the thermal chip module.

10. The device according to claim 1, wherein the device is a genotyping device.

11. The device according to claim 1, wherein the device is an avian sexing device.

12. The device according to claim 1, wherein the egg sampling unit comprises an avian egg tray, a plurality of egg receivers spaced at an egg pitch, and an egg sampling head comprising needles spaced at an egg pitch.

13. The device according to claim 1, wherein the thermal chip module is mobile.

14. The device according to claim 13, wherein the thermal chip module is operatively connected to the egg sampling unit via a rail that permits movement of the thermal chip module to and from the egg sampling unit.

15. The device according to claim 1, wherein the self-contained CLC locations of the thermal chip module are arranged in multiple clusters that are spaced at a pitch configured for receiving the biological samples from the multiple avian eggs.

16. The device according to claim 15, wherein each of the multiple clusters comprises from 2 to 40 self-contained CLC locations.

17. The device according to claim 16, wherein the thermal chip module comprises 84 clusters each comprising 17 self-contained CLC locations.

18. The device according to claim 3, wherein the thermal chip module comprises an upper lid and a lower lid, wherein the upper lid and lower lid comprise holes corresponding to the self-contained CLC locations, wherein the upper lid is fixed to the thermal chip module such that the holes are aligned with the corresponding self-contained CLC locations and the lower lid is mounted on a mechanism that can be actuated to offset the alignment of the holes with the upper lid to close the holes in the upper lid.

* * * * *